(12) United States Patent
Covalin et al.

(10) Patent No.: US 12,318,604 B2
(45) Date of Patent: Jun. 3, 2025

(54) CONTROLLING OR REDUCING STRESS USING AURICULAR NEUROSTIMULATION

(71) Applicant: Spark Biomedical, Inc., Dallas, TX (US)

(72) Inventors: Alejandro Covalin, Los Angeles, CA (US); Navid Khodaparast, Dallas, TX (US); Melanie McWade, Portland, OR (US)

(73) Assignee: SPARK BIOMEDICAL, INC., Dallas, TX (US)

( * ) Notice: Subject to any disclaimer, the term of this patent is extended or adjusted under 35 U.S.C. 154(b) by 0 days.

(21) Appl. No.: 18/540,162

(22) Filed: Dec. 14, 2023

(65) Prior Publication Data

US 2024/0181243 A1     Jun. 6, 2024

Related U.S. Application Data

(63) Continuation of application No. 17/750,109, filed on May 20, 2022, now abandoned.

(51) Int. Cl.
    *A61N 1/04*        (2006.01)
    *A61N 1/36*        (2006.01)

(52) U.S. Cl.
    CPC .......... *A61N 1/0456* (2013.01); *A61N 1/3603* (2017.08); *A61N 1/36036* (2017.08)

(58) Field of Classification Search
    CPC ............. A61N 1/0456; A61N 1/3603; A61N 1/36036; A61N 1/36025; A61N 1/36034
    See application file for complete search history.

(56) References Cited

U.S. PATENT DOCUMENTS

| | | |
|---|---|---|
| 6,610,713 B2 | 8/2003 | Tracey |
| 7,386,347 B2 | 6/2008 | Chung et al. |

(Continued)

FOREIGN PATENT DOCUMENTS

WO     2019014250 A1     1/2019

OTHER PUBLICATIONS

Sailer, et al., Altered reward processing in the nucleus accumbens and mesial prefrontal cortex of patients with posttraumatic stress disorder, Neuropsychologia, 46:11, May 2008, pp. 2836-2844, DOI: 10.1016/j.neuropsychologia.2008.05.022.

(Continued)

*Primary Examiner* — Amanda K Hulbert
*Assistant Examiner* — Natasha Patel
(74) *Attorney, Agent, or Firm* — Finch & Maloney PLLC

(57) ABSTRACT

In an illustrative embodiment, an apparatus for controlling or reducing stress levels includes an ear-mounted device having an earpiece for positioning over a wearer's ear contacting tissue regions surrounding the ear, and electrodes for delivering non-piercing neurostimulation, with first electrode(s) arranged on a first surface of the earpiece to contact a first tissue region, and second electrode(s) are arranged on a second surface to contact a second tissue region. The auricular branch of the vagus nerve or the auriculotemporal nerve is situated beneath the first tissue region. The apparatus includes a controller to deliver therapeutic stimulation pulses via the stimulation device, where the pulses in combination with the positioning of the first electrode(s) and the second electrode(s) are configured to modulate the activity ratio between the sympathetic nervous system and the parasympathetic nervous system, thereby increasing vagal tone.

16 Claims, 14 Drawing Sheets

(56) References Cited

U.S. PATENT DOCUMENTS

| | | | |
|---|---|---|---|
| 7,493,171 | B1 | 2/2009 | Whitehurst et al. |
| 8,204,601 | B2 | 6/2012 | Moyer et al. |
| 8,554,324 | B2 | 10/2013 | Brocke |
| 8,729,129 | B2 | 5/2014 | Tracey et al. |
| 8,755,892 | B2 | 6/2014 | Amurthur et al. |
| 8,914,123 | B2 | 12/2014 | Rigaux |
| 8,918,178 | B2 | 12/2014 | Simon et al. |
| 9,089,719 | B2 | 7/2015 | Simon et al. |
| 9,101,766 | B2 | 8/2015 | Nekhendzy |
| 9,415,220 | B1 | 8/2016 | Spinelli et al. |
| 9,682,236 | B2 | 6/2017 | Degiorgio et al. |
| 9,782,584 | B2 | 10/2017 | Cartledge et al. |
| 1,002,254 | A1 | 7/2018 | Pfeifer |
| 10,130,809 | B2 | 11/2018 | Cartledge et al. |
| 10,155,114 | B2 | 12/2018 | De Ridder |
| 10,207,106 | B2 | 2/2019 | Simon et al. |
| 10,279,178 | B2 | 5/2019 | Cartledge et al. |
| 10,322,062 | B2 | 6/2019 | Brown et al. |
| 10,413,719 | B2 | 9/2019 | Brown et al. |
| 10,426,945 | B2 | 10/2019 | Tyler et al. |
| 10,780,264 | B2 | 9/2020 | Alam |
| 10,828,461 | B2 | 11/2020 | Cartledge et al. |
| 10,857,360 | B2 | 12/2020 | Waclawik |
| 10,912,712 | B2 | 2/2021 | Tracey et al. |
| 2004/0249416 | A1* | 12/2004 | Yun .................. A61N 1/36189 607/2 |
| 2009/0131995 | A1 | 5/2009 | Sloan et al. |
| 2010/0222843 | A1 | 9/2010 | Tass et al. |
| 2014/0121740 | A1 | 5/2014 | Patterson et al. |
| 2014/0266752 | A1 | 9/2014 | John |
| 2015/0174418 | A1 | 6/2015 | Tyler et al. |
| 2016/0263376 | A1 | 9/2016 | Yoo et al. |
| 2016/0279021 | A1 | 9/2016 | Hyde et al. |
| 2017/0087364 | A1 | 3/2017 | Cartledge et al. |
| 2017/0224990 | A1 | 8/2017 | Goldwasser et al. |
| 2017/0312505 | A1* | 11/2017 | Ahmed .................. A61N 1/205 |
| 2017/0368329 | A1 | 12/2017 | Tyler et al. |
| 2018/0085573 | A1 | 3/2018 | Alam |
| 2018/0318585 | A1 | 11/2018 | Pfeifer |
| 2018/0339148 | A1 | 11/2018 | Kong |
| 2019/0046794 | A1 | 2/2019 | Goodall et al. |
| 2019/0111259 | A1 | 4/2019 | De Ridder |
| 2019/0151646 | A1 | 5/2019 | Cakmak |
| 2019/0262229 | A1 | 8/2019 | Brown et al. |
| 2019/0275322 | A1 | 9/2019 | Cartledge et al. |
| 2019/0321623 | A1 | 10/2019 | Huston et al. |
| 2020/0030608 | A1 | 1/2020 | Halpern |
| 2020/0038658 | A1 | 2/2020 | Tyler et al. |
| 2020/0094055 | A1 | 3/2020 | Manogue |
| 2020/0108250 | A1 | 4/2020 | Ireland |
| 2020/0139124 | A1 | 5/2020 | Amurthur |
| 2020/0197707 | A1 | 6/2020 | Covalin |
| 2020/0238085 | A1 | 7/2020 | Khodaparast et al. |
| 2020/0261688 | A1 | 8/2020 | Thoma |
| 2020/0261722 | A1 | 8/2020 | Alataris et al. |
| 2020/0323684 | A1 | 10/2020 | O'Leary et al. |
| 2020/0345970 | A1 | 11/2020 | La Rovere et al. |
| 2021/0001124 | A1 | 1/2021 | Brown et al. |
| 2021/0038879 | A1 | 2/2021 | Pfeifer |
| 2021/0069505 | A1 | 3/2021 | Romine et al. |
| 2021/0077812 | A1 | 3/2021 | Hool et al. |
| 2021/0213286 | A1 | 7/2021 | Covalin et al. |
| 2021/0252278 | A1* | 8/2021 | Hamner ............... A61N 1/0456 |
| 2022/0233860 | A1* | 7/2022 | Hamner ............. A61N 1/36031 |
| 2023/0149703 | A1 | 5/2023 | Covalin et al. |

OTHER PUBLICATIONS

Neylan, Thomas C., Frontal Lobe Moderators and Mediators of Response to Exposure Therapy in PTSD, Am J Psychiatry, 174:12, Dec. 2017, pp. 1131-1133, DOI: 10.1176/appi.ajp.2017.17091056.

Mehta, et al., Inflammation, reward circuitry and symptoms of anhedonia and PTSD in trauma-exposed women, Social Cognitive and Affective Neuroscience, vol. 15, Issue 10, 2020, pp. 1046-1055, DOI: 10.1093/scan/nsz100.

Boukezzi, et al., Posttraumatic Stress Disorder is associated with altered reward mechanisms during the anticipation and the outcome of monetary incentive cues, NeuroImage: Clinical, vol. 25, 102073, 2020, DOI: 10.1016/j.nicl.2019.102073.

Sherin, Jonathan E., and Nemeroff, Charles B., Post-traumatic stress disorder: the neurobiological impact of psychological trauma, Dialogues in Clinical Neuroscience, vol. 13, No. 3, 2011, pp. 263-278.

Somohano, et al., PTSD symptom clusters and craving differs by primary drug of choice, J Dual Diagn., 15(4), 2019, pp. 233-242, DOI: 10.1080/15504263.2019.1637039.

Elman, et al., Reward and aversion processing in patients with post-traumatic stress disorder: functional neuroimaging with visual and thermal stimuli, Translational Psychiatry, 8:240, Nov. 2018, pp. 1-15, DOI: 10.1038/s41398-018-0292-6.

Seidemann, et al., The Reward System and Post-Traumatic Stress Disorder: Does Trauma Affect the Way We Interact With Positive Stimuli?, Chronic Stress, vol. 5, Feb. 25, 2021, pp. 1-11, DOI: 10.1177/2470547021996006.

Torrisi, et al., Therapeutic Challenges of Post-traumatic Stress Disorder: Focus on the Dopaminergic System, Frontiers in Pharmacology, vol. 10, Article 404, Apr. 17, 2019, pp. 1-11, DOI: 10.3389/fphar.2019.00404.

Basner, et al., Continuous and Intermittent Artificial Gravity as a Countermeasure to the Cognitive Effects of 60 Days of Head-Down Tilt Bed Rest, Frontiers in Physiology, vol. 12, Article 643854, Mar. 17, 2021, pp. 1-14, DOI: 10.3389/fphys.2021.643854.

Jenkins, et al., Transcutaneous Auricular Neurostimulation (tAN): A Novel Adjuvant Treatment in Neonatal Opioid Withdrawal Syndrome, Frontiers in Human Neuroscience, vol. 15, Article 648556, Mar. 8, 2021, pp. 1-12, DOI: 10.3389/fnhum.2021.648556.

U.S. Department of Veterans Affairs, Pain Management Opioid Taper Decision Tool, A VA Clinician's Guide, Oct. 2016, IB 10-939 P96820.

Opioid Oral Morphine Milligram Equivalent (MME) Conversion Factors, Aug. 2017. Available at: https://www.cms.gov/Medicare/Prescription-Drug-coverage/PrescriptionDrugCovContra/Downloads/Opioid-Morphine-EQ-Conversion-Factors-Aug-2017.pdf.

U.S. Department of Health and Human Services, Centers for Disease Control and Prevention, Calculating Total Daily Dose of Opioids for Safer Dosage. Available at: https://www.cdc.gov/drugoverdose/pdf/calculating_total_daily_dose-a.pdf.

Gradus et al. 2010. "Acute Stress Reaction and Completed Suicide," International Journal of Epidemiology 39 (6): 1478-84.

"Transcutaneous Auricular Neurostimulation (tAN™) to Aid in the Reduction of Symptoms Associated with Opiod Withdrawal," Spark Biomedical Whitepaper, 2021.

Shin et al., "Hippocampal activation of 5-HT1B receptors and BDNF production by vagus nerve stimulation in rats under chronic restraint stress," European Journal of Neuroscience, 50:1820-30 (2019).

International Search Report and Written Opinion mailed Dec. 15, 2022 in International PCT Application No. PCT/US2022/030386.

"Prevent." Merriam-Webster.com Dictionary, Merriam-Webster, https://www.merriam-webster.com/dictionary/prevent. Accessed Aug. 22, 2022. (Year: 2022).

* cited by examiner

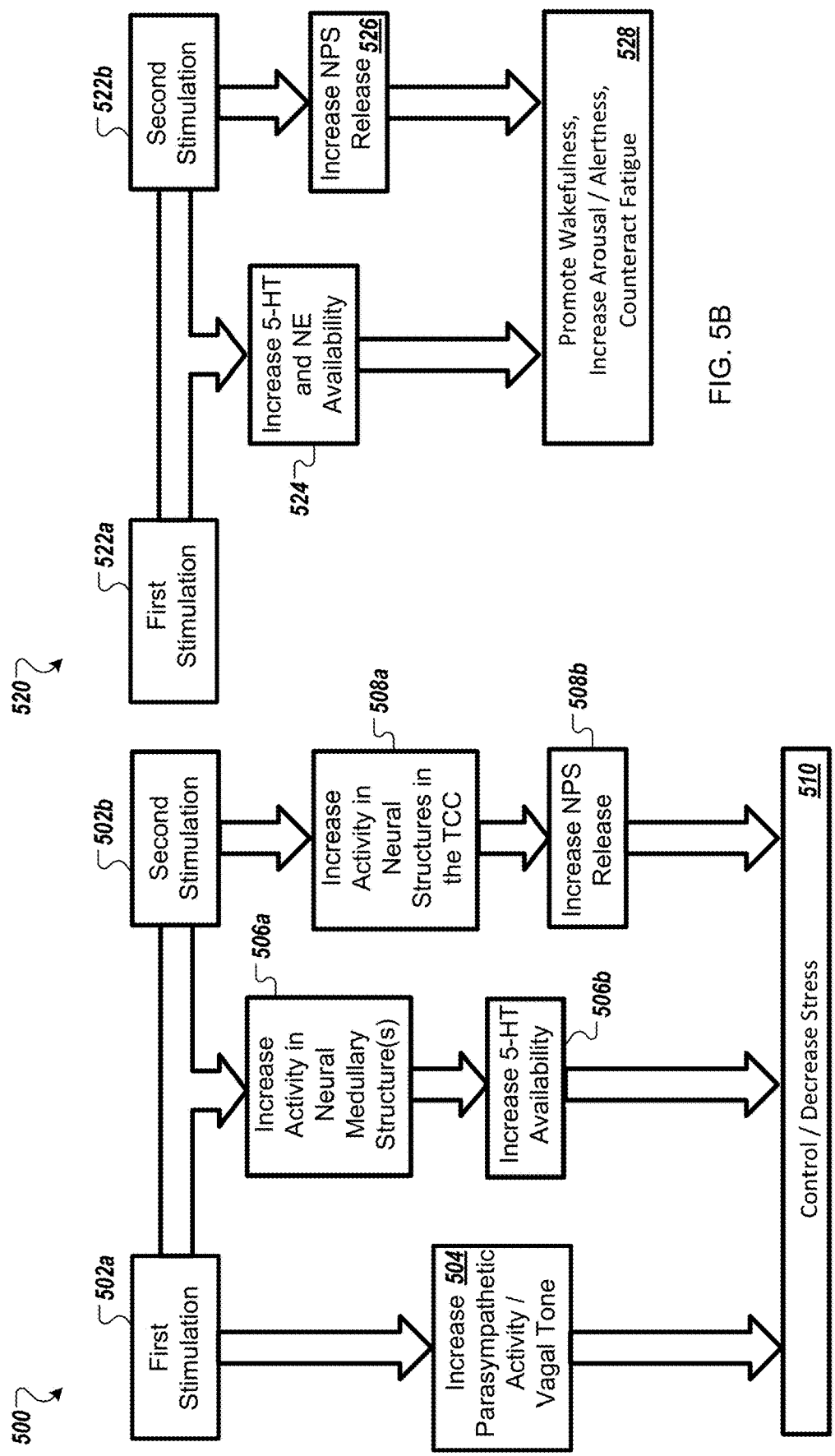

CONTROLLING OR REDUCING STRESS USING AURICULAR NEUROSTIMULATION

CROSS-REFERENCE TO RELATED APPLICATIONS

This application is a continuation of and claims priority to U.S. patent application Ser. No. 17/750,109 entitled "Devices and Methods for Treating Stress and Improving Alertness Using Electrical Stimulation" and filed May 20, 2022.

This application is related to the following: U.S. patent application Ser. No. 18/094,313 entitled "Devices and Methods for Treating Stress and Improving Alertness Using Electrical Stimulation," filed Jan. 6, 2023 (now U.S. Patent Publication No. 2023/0149703), which is a continuation-in-part of, and claims priority to, U.S. patent application Ser. No. 17/832,437 entitled "Devices and Methods for the Treatment of Substance Use Disorders," filed Jun. 3, 2022 (now U.S. Pat. No. 11,623,088); and U.S. patent application Ser. No. 17/219,712 entitled "Devices and Methods for Treating Cognitive Dysfunction and Depression Using Electrical Stimulation," filed Mar. 31, 2021 (now U.S. Pat. No. 11,351,370), which is a continuation-in-part of, and claims priority to, U.S. patent application Ser. No. 16/846,220 entitled "Devices and Methods for Reducing Inflammation Using Electrical Stimulation," filed Apr. 10, 2020 (now U.S. Pat. No. 10,967,182), which is a continuation-in-part of, and claims priority to, U.S. patent application Ser. No. 16/510,930 entitled "Device and Method for the Treatment of Substance Use Disorders," filed Jul. 14, 2019 (now U.S. Pat. No. 10,695,568).

All above identified applications are hereby incorporated by reference in their entireties.

BACKGROUND

Events that trigger stress are generally called stressors; individuals react differently to similar as well as to dissimilar stressors. In general, stressors can be divided into two main categories or types: physical and psychological. Physical stressors include a physical threat to bodily homeostasis; for example, bleeding profusely or having an infection. Psychological stressors include a perceived threat, which, as such, needs to be interpreted; for example, being in front of a hungry tiger, running late for a meeting, or feeling pressure to properly perform a task. Stress is part of normal life, and a healthy response to a stressor may be demonstrated by an anticipatory phase, a peak response during the event, and a return to baseline.

Even though stress is part of life, at some level of stress (which may be different for everyone at a particular time), performance generally becomes negatively affected. The effects of stress on performance can manifest in physical, cognitive, emotional, and/or behavioral impairments that affect a number of areas of life, such as decision-making, perception, and cognition. Individuals under stress tend to consider a reduced pool of available options, oftentimes resulting in a suboptimal decision, and, in some cases, a potentially risky or dangerous one. This suboptimal decision is not only driven by a lack of a thorough analysis but also by a reduced number of perceived external cues. This reduction of perceived external cues is sometimes referred to as "tunnel vision," although the perception reduction is not limited to vision. In addition to only considering a limited pool of options when making a decision, people under stress, tend to process information slower; in fact, a study found that individuals under stress may take as much as twice the amount of time to complete the same task when a stressor is introduced.

As stated, stress tends to reduce people's perception field thus not allowing all available information to be considered while consciously or unconsciously responding to external stimuli. This scenario often leads to mistakes and accidents. For example, drivers experiencing a reduced perception field may be more apt to cause accidents or injuries. In other examples, stress may cause an athlete, an air traffic controller, or a stockbroker to make mistakes, in particular when performance demands are at their highest.

In many cases, the pressure felt through recognizing that a non-ideal action or response could lead to a highly undesirable outcome will lead to high levels of stress. Pressure-induced stress, in some examples, may be experienced by professional athletes during competition, including those performing electronic sports (Esports), or by military operators, including those operating unmanned vehicles.

A large percentage of the population has reported feeling under stress on a regular basis; the perception of stress tends to increase when working long hours, working under pressure, and/or not sleeping enough.

In some cases, people develop what is known as an Acute Stress Reaction (ASR), also known as Acute Stress Disorder (ASD). If the ASR is prolonged or the stressor causing it is persistent or reoccurring, a person suffering from an ASR may go on to develop Post-Traumatic Stress Disorder (PTSD). In addition to the reactions/symptoms to stress described above, ASR symptoms may also include fatigue, restlessness, panic, irritability, rage, flashbacks, nightmares, intrusive memories, confusion, avoidance of reminders of the event (e.g., avoiding people, conversations, places, etc.), difficulty remembering the event, reckless or aggressive behavior (which may be self-destructive), feeling emotionally numb and detached from others, an inability to experience positive emotions, anxiety, sleep disturbances, and difficulty concentrating. Additionally, some of the physical symptoms of an ASR may include chest pain, pounding heart or palpitations, feeling sick (e.g., nausea), abdominal pain, loss of appetite, headaches, and/or difficulty breathing. In the beginning, ASR may lead to performance issues, however, ASR can also manifest into a serious medical problem. ASR is a risk factor for completed suicide. In one study, for example, it was found that individuals diagnosed with ASR followed through with completed suicide at a rate of 10 times of those who were not diagnosed with ASR. See Gradus et al. 2010. "Acute Stress Reaction and Completed Suicide." International Journal of Epidemiology 39 (6): 1478-84.

ASRs are more common (or at least more commonly diagnosed) in some situations than in others. For example, ASR diagnoses are common in the military and can be life threatening to the individual experiencing it as well as to the team working with the individual. In the military, ASRs may also be referred to as Combat Stress Reaction (CSR) and Operational Stress Reaction (OSR) or together as Combat and Operational Stress Reactions (COSRs). Often, the conditions of operational environments increase exposure to severely stressful situations and prolong the duration of time soldiers must cope with severe stressors, thereby putting personal safety and mission success at risk. Further, many battlefield situations do not allow for the affected soldier to be close enough to trained personnel to avert adverse effects from an ASR event.

Individuals under long-term or chronic stress tend to develop pathological conditions, including cardiovascular disease, muscle pain, stomach and intestinal problems, decreased fertility, and reduced immune system strength.

Long-term stress can also lead to feelings of anger, anxiety, fatigue, depression, as well as sleep problems. Furthermore, as stated previously, long-term exposure to a stressor or stressors can lead to the development of PTSD; patients with PTSD have shown a greater propensity to alcohol and opioid abuse. See Bilevicius, Elena et. al. 2018. "Posttraumatic Stress Disorder and Chronic Pain Are Associated with Opioid Use Disorder: Results from a 2012-2013 American Nationally Representative Survey." Drug and Alcohol Dependence 188 (July): 119-25. Additionally, long-term stress may also lead to burnout. Stress is a well-known risk factor in the development of addiction (e.g., substance use disorder) and in addiction relapse vulnerability.

Burnout manifests as emotional exhaustion, physical fatigue, diminished professional efficacy, cognitive impairments, feelings of ineffectiveness, detachment, and cynicism. Burnout is generally the result of a sustained or prolonged psychosocial stress exposure in which a mismatch between demands and resources exists or it is believed by the sufferer to exist. For example, when the personal emotional, cognitive, and physical resources are not, or are perceived to not be sufficient to overcome the demands of a situation or an environment. Available data regarding development of burnout supports an initial hyperactive stress response (in both the Hypothalamic-Pituitary-Adrenal (HPA) axis and the sympathetic system) followed by physiological exhaustion resulting in an impaired physiological response (hyporeactivity of the HPA axis).

Reducing and/or controlling stress to an individual's manageable level and not allowing stress to become chronic, could lead to a more desirable and faster response to a scenario or event, as well as to a better decision-making process, better overall performance and the prevention of burnout. Furthermore, reducing and/or controlling stress could help prevent undesired health consequences as well positively influencing life span. Effectively reducing and/or controlling stress is dependent on the immediacy of an intervention.

SUMMARY OF ILLUSTRATIVE EMBODIMENTS

Chronic exposure to stressors leads to continuously higher perceived stress. Stress and aging have been shown to be positively correlated; interestingly, studies have shown that stress as well as inflammation (including low-level inflammation) influence telomere attrition. Telomeres are the last portion of the chromosomes and protect the DNA. With each cell replication/division, the telomere length (TL) tends to decrease. TL has been linked to lifespan and has been used as a biomarker of cellular aging. An unhealthy response to acute stress (e.g., an exaggerated response, such as a very long anticipatory response or a long return to baseline), may result in detrimental changes in telomere regulation, including problems with telomerase activity (TA). Telomerase is an enzyme which activity counteracts telomere shortening. For instance, an autonomic overreaction has been correlated with an increased cortisol reactivity to stressors, with diminished immune cell function, and shorter TL. Perseverative cognition (e.g., rumination and worriedness), which can increase the stress reaction and prolong the recovery time to baseline has also been associated with shorter TL. An overreaction in the form of longer, or stronger/exaggerated anticipatory threat appraisals to acute stressors is one example of perseverance cognition.

The profile of an acute stress reaction is mainly affected by allostatic cases, for example, basal levels of inflammation and hormones as well as baseline autonomic and neuroendocrine activity. A prolonged stress reaction and/or repeated exposures to a particular stressor may lead to disturbed allostatic states. Shorter TL as well as lower TA have been linked to a decreased vagal tone, increased basal levels of cortisol, oxidative stress, and inflammation.

Among healthy individuals, the two branches of the autonomic nervous system (ANS), i.e., the sympathetic nervous system (SNS) and the parasympathetic nervous system (PNS) are in a dynamic balance. This allows for a fast and efficient response to a challenge (internal or external) followed by a fast and efficient return to baseline when the challenge is over. At high levels of stress and/or under chronic stress, the dynamic balance between the SNS and the PNS is lost, resulting in excessive demands and insufficient recovery. This stress-related autonomic imbalance is the result of a hyperactive SNS and a hypoactive PNS. The general response to both physical and psychological stress is activation of the sympathetic nervous system with inhibition of the parasympathetic nervous system. Interestingly, studies have shown that a higher baseline parasympathetic activity leads to a more controlled stress response. A higher parasympathetic activity allows to a faster counteraction of the stress response and a rapid return to baseline after the challenge (i.e., the stressor) has passed. One way to increase parasympathetic activity is to increase vagal tone (e.g., increasing vagal activity). For example, increasing vagal tone when stress is high enough to start negatively impacting performance would lower the stress response and would bring stress to a manageable level, i.e., to a level at which performance is no longer impacted.

Given the above, the inventors recognized that controlling or reducing stress levels as well as not allowing a decreased vagal tone would be highly desirable. In one aspect, the present disclosure relates to addressing stress through affecting the balance of the ANS by modulating the activity ratio between the SNS and the PNS. In some embodiments, modulating the activity ratio between the SNS and PNS involves activating vagal and/or auriculotemporal nerve structures, leading to an increase in vagal activity and thus vagal tone. This may be achieved not only by directly stimulating the above-mentioned nerve structures but also as a consequence of the activation of efferent descending pathways from the NTS and the nucleus ambiguus (NA).

As mentioned above, fatigue or feeling fatigued or extremely fatigued is one of the symptoms or consequences of stress. Fatigue can be said to be or to manifest as a lack of alertness. Wakefulness is a state in which an individual can perceive external stimuli and interact with their surroundings and their environment. The degree of vigilance and alertness during wakefulness is called arousal, and it corresponds to the level of: (a) responsiveness to sensory inputs, (b) emotional reactivity, and (c) cognitive processing.

The inventors recognized that controlling or reducing levels of fatigue as well as encouraging alertness would be highly desirable. In one aspect, the present disclosure relates to increasing both norepinephrine (NE) and neuropeptide S (NPS) as it activates the locus coeruleus (LC), trigeminal areas and the parabrachial nucleus (PbN). NPS activity is paradoxical as it acts as an anxiolytic and yet increases arousal.

Furthermore, studies have shown stress can negatively affect neuroplasticity by altering hippocampal function. This functional alteration is similar to that seen in cases of depression. The neural centers forming the circuit involved in the stress response are also the ones involved in the physiology of depression. Interestingly, stressed individuals respond positively when treated with antidepressants such as selective serotonin (5-HT) reuptake inhibitors (SSRI). Thus, antidepressant treatments targeting the neural circuit that increase 5-HT have a positive effect on stress. Neuroplasticity is key for learning and memory and brain-derived neurotrophic factor (BDNF) is crucial for neuroplasticity; high stress levels have been shown to negatively impact BDNF availability.

The inventors recognized that treating depression through 5-HT increase would be a highly beneficial augmentation to treating stress. In one aspect, the present disclosure relates to increased activity in neural medullary structures such as, amongst others, the nucleus tractus solitarius (NTS). This activity increase in neural medullary structures triggers a cascade of neural activity in other brain areas which have direct and indirect connections to these neural medullary structures. For example, increasing activity in the neural medullary structures may result in increasing the availability of monoamine neurotransmitters such as Serotonin (5-HT) as well as endogenous release of neuropeptides such as endorphins. This increase in endorphins triggers further activity in neuronal populations in yet other brain regions, for example, in populations of GABAergic interneurons in the ventral tegmental area (VTA), which are inhibited by the endorphins. This inhibition of GABAergic interneurons leads to an increase in the release of dopamine form dopaminergic neurons also located at the VTA. As a result, there is a net increase in dopamine availability. An increasing activity in the trigeminocervical complex (TCC) may result not only in an activity increase in some medullary neural structures but also in an increase in the availability of NE and in an improvement in BDNF availability.

It has been shown that acute stress promotes both fibrinolysis and platelet aggregation which in most cases counteract each other. Fibrinolysis is promoted via an increased release of tissue plasminogen activator (tPA) from endothelial and chromaffin cells. When the balance between fibrinolysis and platelet aggregation is disrupted, stressed individuals are prone to either bleeding or thrombosis. Individuals under stress with hemostatic disorders such as Factor VIII deficiency (i.e., hemophilia) as well as those with Von Willebrand disease are prone to bleeding. Interestingly, a bleeding control method via stimulation of vagal and/or trigeminal structures has been proposed by researchers from the Feinstein Institute. The bleeding control method is described, for example, in U.S. Pat. No. 8,729,129 to Tracey et al.; U.S. Pat. No. 10,912,712 to Tracey et al.; U.S. Patent Application Publication No. 2020/0094055 to Manogue; and U.S. Patent Application Publication No. 2019/0321623 to Huston et al., hereby incorporated by reference in their entireties.

The inventors recognized that treating stress reaction would be a highly beneficial augmentation to treating bleeding control. In one aspect, the present disclosure relates to reducing likelihood of bleeding under stressful situations and/or speeding the stoppage of bleeding through vagal and/or trigeminal stimulation in combination with neurostimulation treatment to reduce stress reaction.

The forgoing general description of the illustrative implementations and the following detailed description thereof are merely exemplary aspects of the teachings of this disclosure and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings:

FIG. 5A illustrates example mechanisms for using electrical stimulation to control and/or decrease stress;

FIG. 5B illustrates example mechanisms for using electrical stimulation to promote wakefulness, increase arousal/alertness, and counteract fatigue;

DETAILED DESCRIPTION OF ILLUSTRATIVE EMBODIMENTS

Figure 1A:
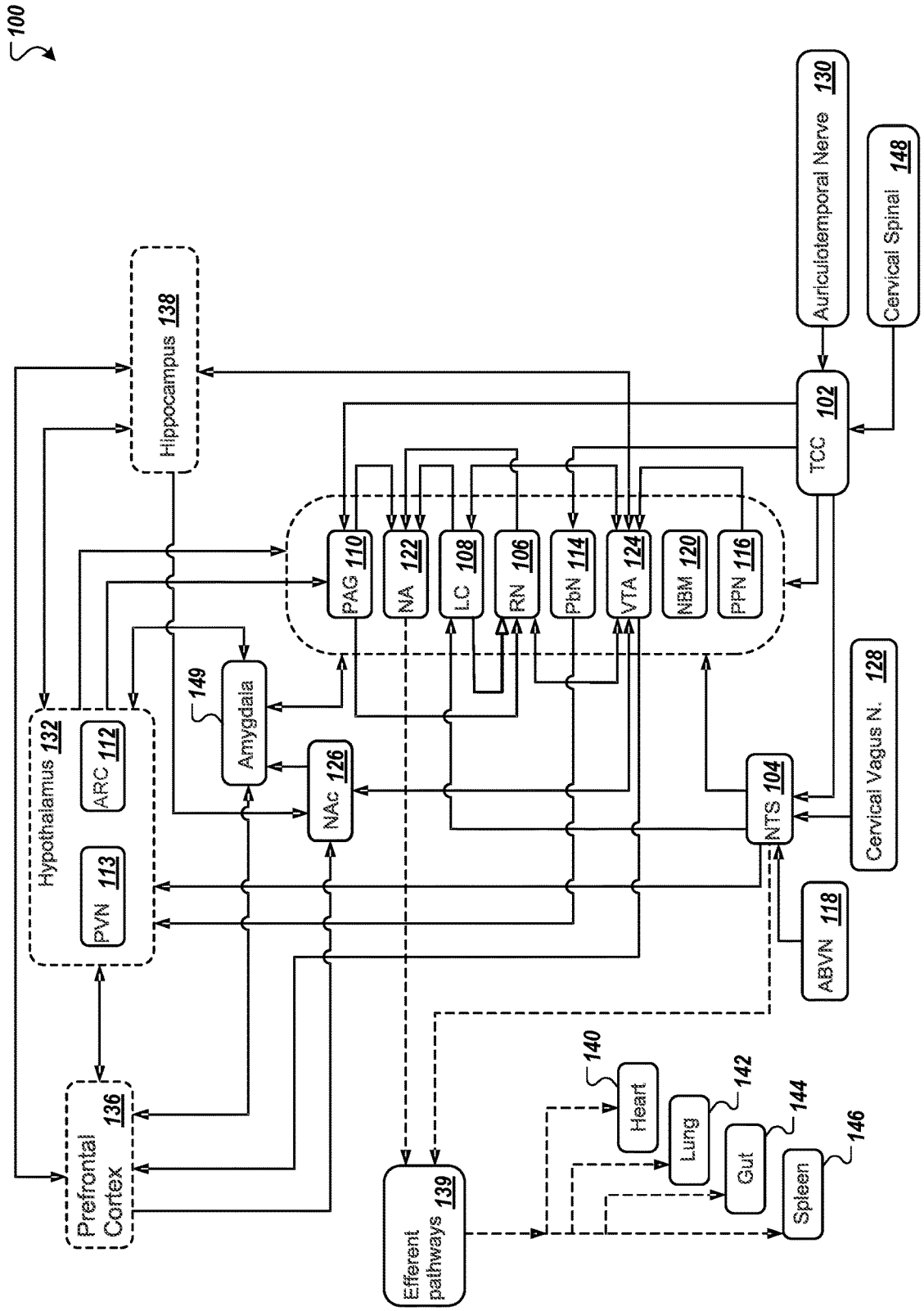
FIGS. 1A and 1B are drawings identifying example neural structures and pathways for delivering therapeutic treatment using an auricular therapeutic device.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

In some implementations, treatment systems, devices, and methods for stimulation of neural structures on and surrounding a patient's ear are designed for providing stimulation without piercing the dermal layers on or surrounding the ear (e.g., transcutaneous stimulation). Electrodes may be frictionally and/or adhesively retained against the skin on and surrounding the patient's ear to target various nerve structures. The electrodes may have a substantial surface area in comparison to prior art systems relying upon dermal-piercing electrodes, such that multiple nerve terminals are stimulated by a single electrode during therapy. For example, a number of nerve terminals may be situated directly beneath and/or beneath and closely adjacent to the skin upon which the electrode is positioned. By targeting multiple nerve terminals, in some embodiments, positioning of each electrode does not necessarily need to be precise. Therefore, for example, a patient or caregiver may be able to apply and remove the device as desired/needed (e.g., for sleeping, showering, etc.). Further, targeting multiple nerve terminals is advantageous since stimulating multiple branches of a nerve elicits a stronger response than stimulating a single branch, which is the case when using pinpoint electrodes such as needle electrodes.

Although example implementations described herein relate to auricular transcutaneous stimulation, transcutaneous access to target nerve structures, such as vagal and trigeminal nerves and/or nerve branches, is not limited to the auricular branch of the vagus nerve (ABVN) and the auriculotemporal nerve. For example, the vagus nerve, as it ascends inside the carotid sheath along the neck, approaches the subcutaneous region. Trigeminal nerves approach the subcutaneous region at several locations in the face; for example, the supraorbital nerve, supratrochlear nerve, infratrochlear nerve, the palpebral branch of the lacrimal nerve, the external nasal nerve, the infraorbital nerve, the zygomaticofacial nerve, the zygomaticotemporal nerve, the mental nerve, and the buccal nerve are potential trigeminal targets to deliver transcutaneous stimulation. A device enabling positioning of electrodes against a subject's skin such that any of these branches is stimulated, for example, may trigger responses related to trigeminal stimulation described below. In illustration, a device enabling stimulation of one or more of the above-noted branches may be used to reduce bleed time and/or bleed volume when stimulating in a prophylactic fashion and/or after an injury that has caused bleeding to occur. For example, a device such as the one described by Simon et al., in U.S. Pat. No. 10,207,106 could be utilized to trigger a vagal response. In a similar manner, the device such as that described by Rigaux in U.S. Pat. No. 8,914,123 can be used to trigger such responses. Furthermore, it is recognized that both devices could be used simultaneously or in an alternative manner to elicit a vagal, a trigeminal, or a trigeminal-vagal response.

In some implementations, methods described herein for stimulation of neural structures on and surrounding a patient's ear may be applied using devices designed for providing percutaneous stimulation. For example, electrodes having tissue-penetrating portions and/or electrodes designed to penetrate tissue (e.g., needle electrodes) may be inserted in a minimally invasive manner (e.g., through at least a top dermal layer of a patient's skin). An example percutaneous auricular stimulation device is the P-STIM® device by Biegler GmbH, described, for example, in U.S. Pat. No. 10,058,478 to Schnetz et al., incorporated herein by reference in its entirety. Percutaneous stimulation, in other embodiments, may be performed at other locations on a subject's skin, for example including the regions described above in relation to transcutaneous stimulation.

Figure 1B:
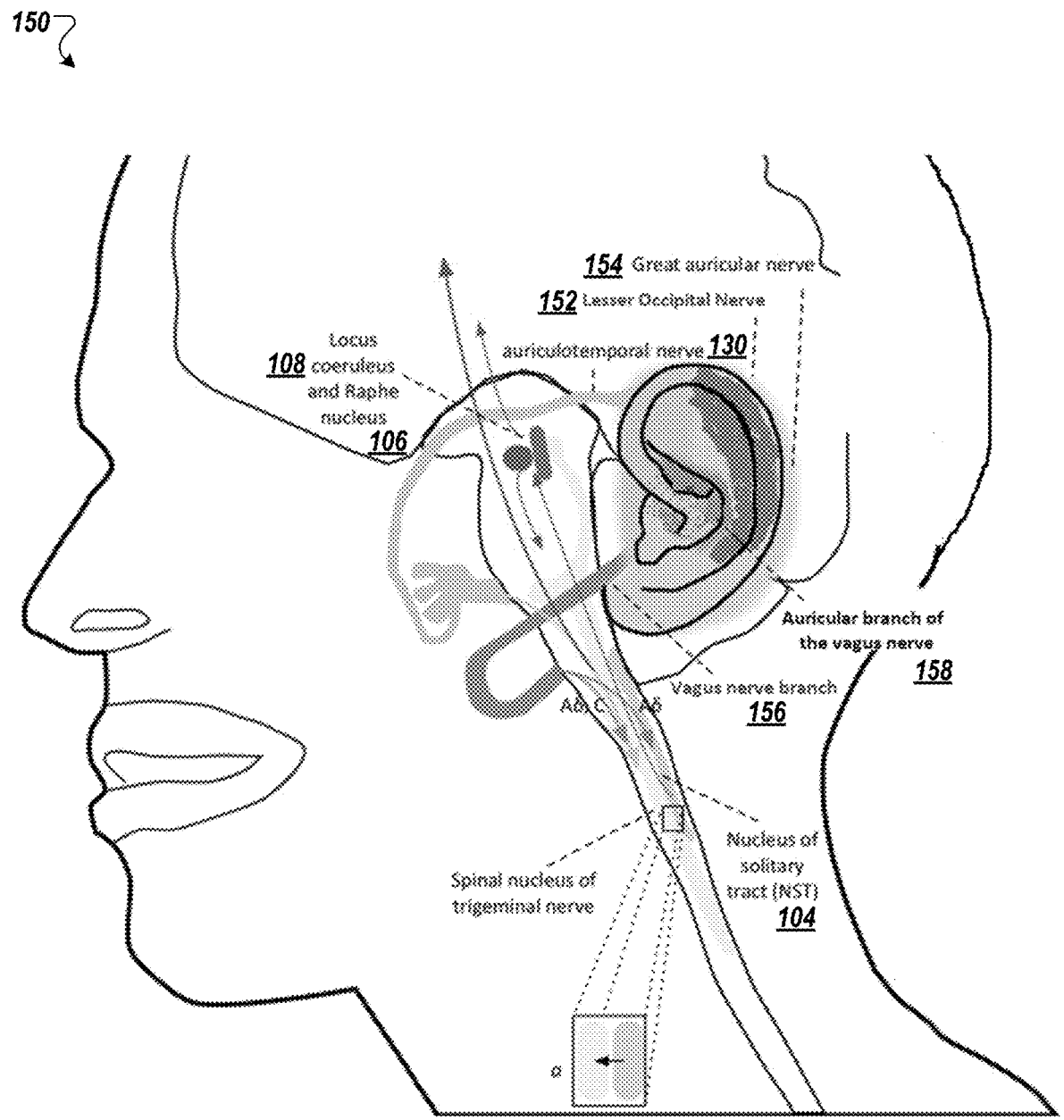

FIGS. 1A and 1B illustrate example neural structures and pathways useful in embodiments disclosed herein for deriving benefits through nerve stimulation. Turning to FIG. 1A, the Nucleus Tractus Solitarius (NTS) 104 receives afferent connections from many areas including the Trigeminocervical Complex (TCC) 102, the cervical vagus nerve 128, as well as from the auricular branch of the vagus nerve (ABVN) 118. The TCC 102 is a region in the cervical spinal cord in which spinal cervical nerves from C1, C2, and C3 converge with sensory trigeminal fibers. In the region of the TCC 102, the trigeminal and occipital fibers synapse, including the Auriculotemporal Nerve 130, the lesser occipital nerve 152 (of FIG. 1B), and the greater auricular nerve 154 (of FIG. 1B) (e.g., Cervical Spinal 148). The TCC 102 projects to multiple areas in the brain stem including, but not limited to parts of the Raphe nuclei (hereafter Raphe Nucleus (RN) 106), the Locus Coeruleus (LC) 108, Periaqueductal Gray (PAG) 110, Nucleus Basalis (NBM) 120, the Nucleus Ambiguus (NA) 122, the Ventral Tegmental Area (VTA) 124, the Nucleus Accumbens (NAc) 126, and Parabrachial nucleus (PbN) 114. The NTS 104 among others, also projects to the RN 106 the LC 108, and the PAG 110 as well as to higher centers like the hypothalamus 132, including into the Arcuate Nucleus (ARC) 112 which receives its majority of non-intrahypothalamic afferents from the NTS 104. Cells in the ARC 112 are the main source of endorphins in the Central Nervous System (CNS).

The medulla oblongata (medulla) is the lower region of the brainstem containing important neuronal structures (nuclei) modulating, for example, several important involuntary actions such as respiration, heart rate, and blood pressure. The medulla contains several important nuclei (medullary nuclei) such as the NTS 104, the spinal trigeminal nucleus, the NA 122, and at least some of the RN 106. Additionally, many interconnections exist amongst different brainstem nuclei (e.g., PAG 110, LC 108, RN 106, NBM 120, PbN 114, Pedunculopontine Nucleus (PPN) 116, NA 122, VTA 124, NAc 126). For example, the LC 108, PAG 110, and RN 106 project to the NA 122, and the PPN 116 projects into the VTA 124. The VTA 124, in turn, projects to the Prefrontal Cortex 136, being interconnected with the hypothalamus 132 and the hippocampus 138. The VTA 124 projects directly to the hippocampus 138 as well. The hippocampus 138, in turn, projects to the NAc 126 and interconnects with the hypothalamus 132.

Figures 3A, 3B:
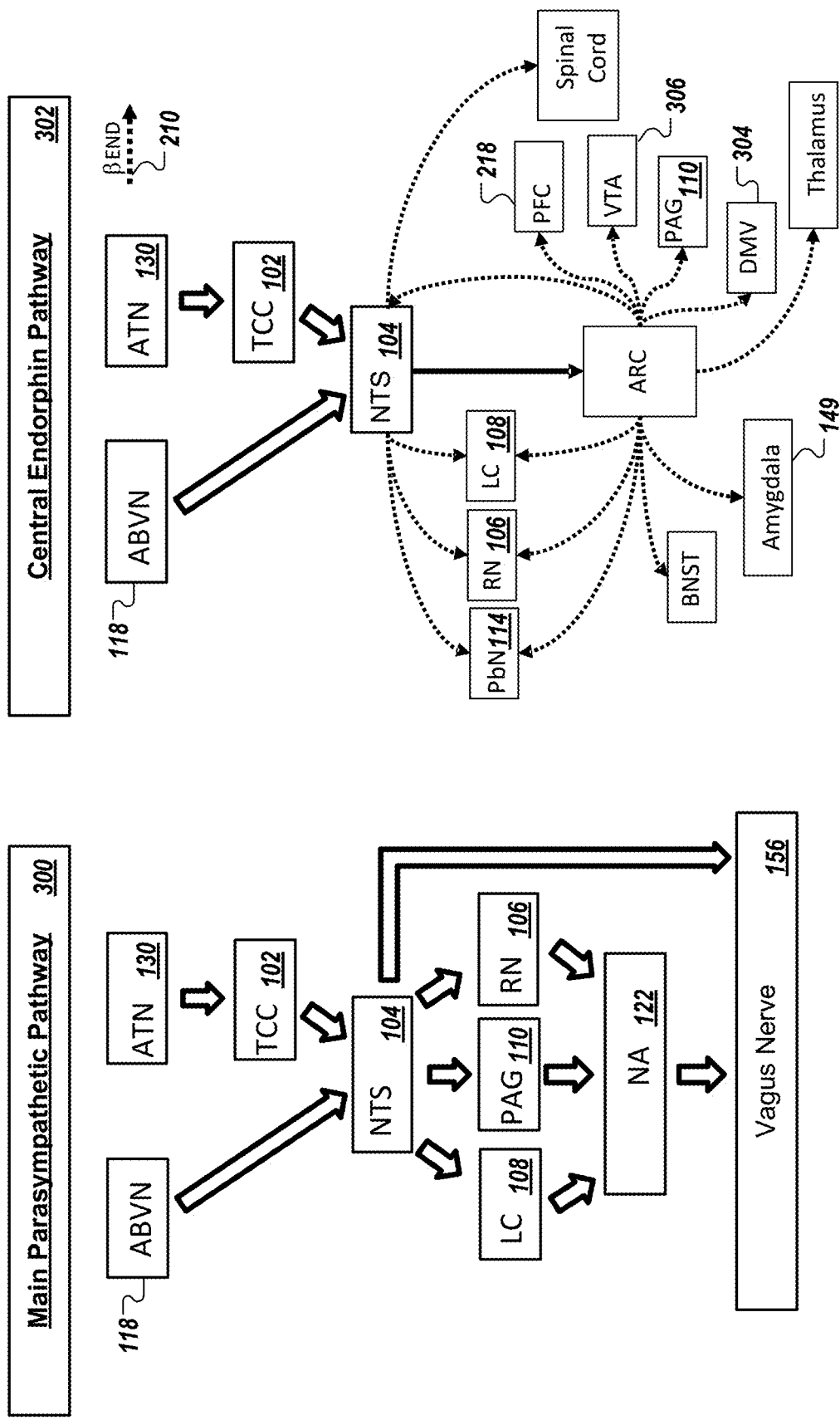
FIG. 3A illustrates example connections of the main parasympathetic pathway.
FIG. 3B illustrates example connections of the central endorphin pathway.

The following table presents a listing of opioid receptors in the central nervous system:

gen absorption can be increased at the lungs 142 by increasing the compliance of the bronchi tissue and thus increasing the oxygen transport availability therefore increasing the potential for more oxygen to be absorbed into the blood; gut motility can be increased by descending pathways originating in the dorsal motor nucleus of the vagus nerve (DMV) 304 of FIG. 3B; since DMV activity is modulated by NTS activity, motility in the gut 144 can be affected by modulating the activity in the NTS 104; and a decrease in circulating pro-inflammatory cytokines can be achieved by modulating spleen 146 activity via NTS 104 descending pathways.

Turning to FIG. 1B, as shown in a diagram 150, the vagus nerve 156 is a cranial nerve that which on its path can be located adjacent to the carotid artery in the neck. Direct stimulation of the vagus nerve 156 activates the nucleus tractus solitarius (NTS) 104, which has projections to nucleus basalis (NBM) 120 and locus coeruleus (LC) 108. The NBM 120 and LC 108 are deep brain structures that release acetylcholine and norepinephrine, respectively, which are pro-plasticity neurotransmitters important for

TABLE 1

| Receptor | Expression/Distribution | Cell Types | Endogenous Ligands (affinity) |
|---|---|---|---|
| MOR | Amygdala 149, thalamus, periaqueductal gray 110, locus coeruleus 108, nucleus raphe magnus, mesencephalon, habenula, hippocampus 138, some brainstem nuclei | GABAergic Glutamatergic | β-endorphin (High) enkephalins (Med) Dynorphin (Low) |
| KOR | Basal anterior forebrain, olfactory tubercle, striatum (caudate putamen and NAc 126), preoptic area, hypothalamus 132, pituitary | Dopaminergic Glutamatergic GABAergic | Dynorphin (High) β-endorphin (Low) enkephalins (Low) |
| DOR | Olfactory tract, cortices, including whole neocortex and regions of the amygdala 149 that derive from the cortex (basolateral, cortical, and median nuclei of the amygdala 149), striatum | GABAergic Dopaminergic | β-endorphin (High) enkephalins (High) Dynorphin (Low) |
| NOP | Periaqueductal gray 110, thalamic nuclei, somatosensory cortex, rostral ventral medulla, spinal cord, dorsal root ganglia, VTA 124, NAc 126, PFC, central amygdala, lateral hypothalamus | Dopaminergic | Orphanin FQ/ nociceptin (High) |

MOR/KOR/DOR = μ/κ/δ-opioid receptor; NOP = nociception/orphanin FQ receptor; NAc = nucleus accumbens; PFC = prefrontal cortex; VTA = ventral tegmental area.
Affinity is presented in parenthesis.

These connections make this neural circuit extremely important for modulating pain, as production of endorphins, enkephalins, and dynorphins are modulated by this circuit. In addition, this neural circuits are crucial for learning and memory as well as for arousal and wakefulness. For example, an interaction between norepinephrine, produced by activity in the Locus Coeruleus (LC) 108, Serotonin (5-HT), produced by activity in the RN 106, and Acetylcholine (ACh) produced by activity in the Pedunculopontine Nucleus (PPN) 116 or NBM 120 is extremely important for memory and learning. Arousal and wakefulness are modulated, amongst others, by catecholamines in the brain, such as norepinephrine and dopamine.

There are descending indirect connections (e.g., via efferent pathways 139) going to the heart 140, lungs 142, gut 144, and spleen 146. Indirect connections include connections where there is at least one synapse elsewhere before reaching the target. This means that modulating the activity of these neural circuits can affect the respective organs. In particular, heart rate can be modulated (e.g., heart rate can be decreased and heart rate variability can be increased); oxylearning and memory. Stimulation of the vagus nerve 156 using a chronically implanted electrode cuff is safely used in humans to treat epilepsy and depression and has shown success in clinical trials for tinnitus and motor impairments after stroke. The auricular branch of the vagus nerve 158 innervates the dermatome region of outer ear, being the region known as the cymba conchae one of the areas innervated by it. Non-invasive stimulation of the auricular branch of the vagus nerve 158 may drive activity in similar brain regions as invasive vagus nerve stimulation. Auricular neurostimulation has proven beneficial in treating a number of human disorders.

Figure 2B:
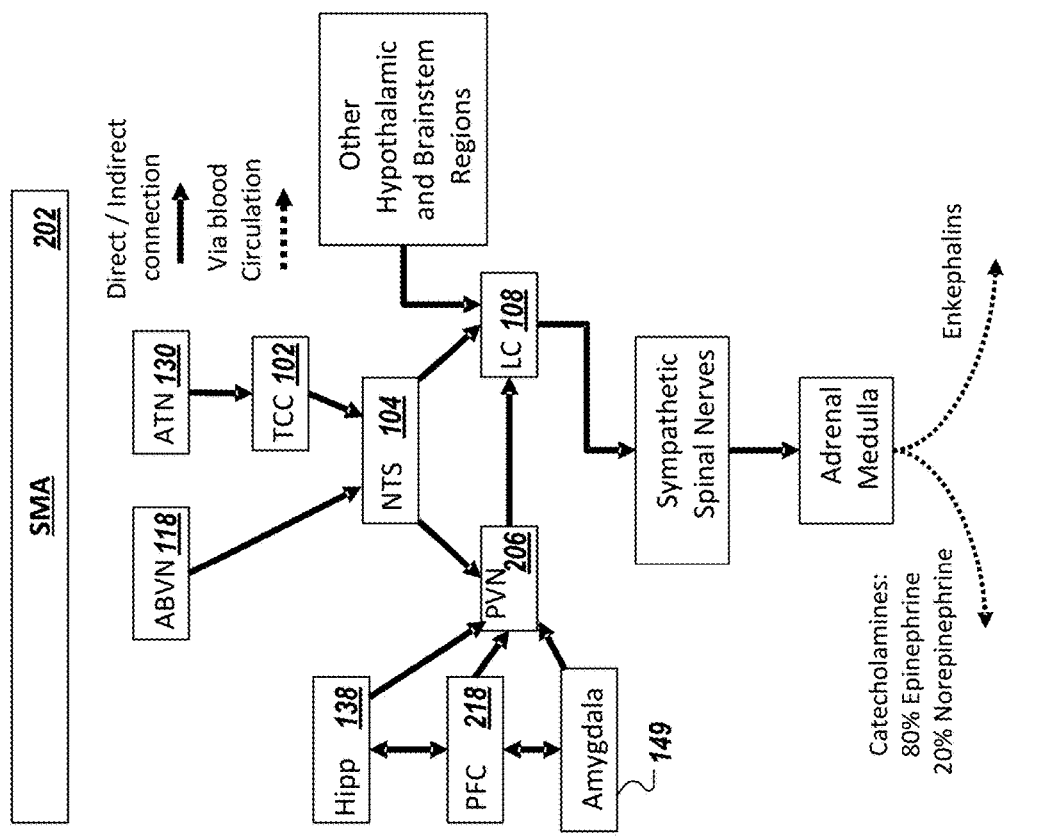
FIG. 2B illustrates example connections of the Hypothalamic-Pituitary-Adrenal (HPA) Axis pathway.
Figure 2A:
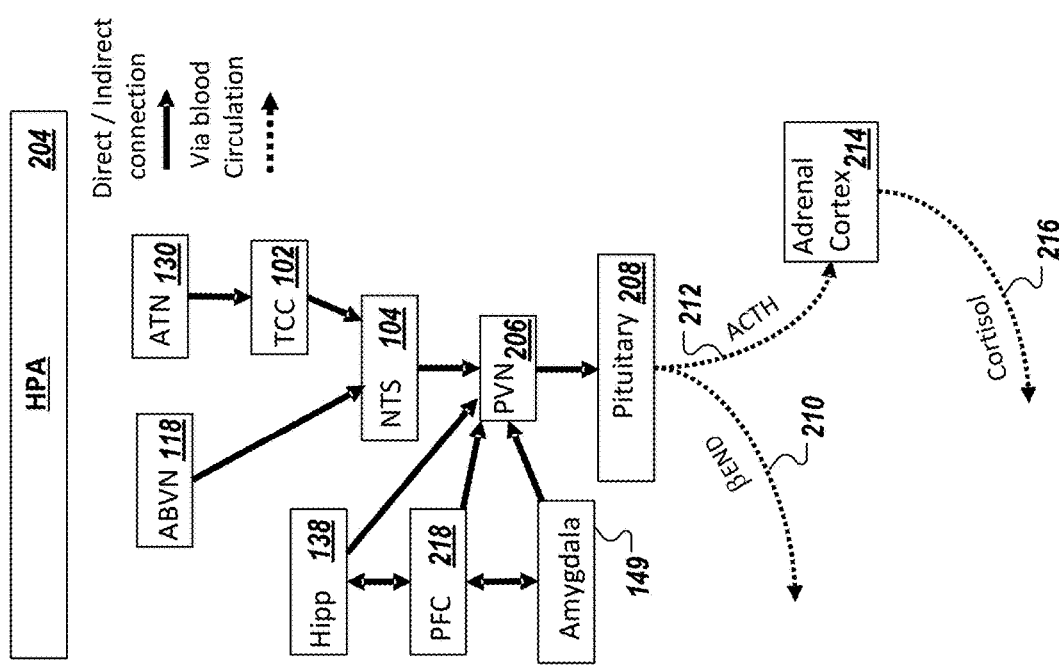
FIG. 2A illustrates example connections of the Sympathetic-Adrenomedullary (SMA) Axis pathway.

Turning to FIG. 2A and FIG. 2B, the response to a stressor, (i.e., the stress response) is carried out via two main pathways: the Sympathetic-Adrenomedullary (SMA) Axis 202 and the Hypothalamic-Pituitary-Adrenal (HPA) Axis 204. Although many brain regions or nuclei are involved in the stress response, the Locus Coeruleus (LC) 108 and the Paraventricular Hypothalamic Nucleus (PVN) 206 (PVN 113 of FIG. 1A) are the two main drivers of these pathways.

The LC 108 is the main producer of Norepinephrine (NE) in the Central Nervous System (CNS) and is one of the main drivers of the SNS. In response to a stressor, the LC 108 releases NE.

In responding to a stressor, the PVN 206 produces, amongst others, Corticotropin (also written as Corticotrophin) Releasing Hormone (CRH), also known as Corticotropin Releasing Factor (CRF). CRH is delivered to several brain nuclei, including the LC 108, as well as to the pituitary gland 208 which consequently releases, amongst others, B-endorphins 210 and adrenocorticotropic hormone (ACTH) 212 into the blood steam. The circulating ACTH 212 reaches the adrenal gland (adrenal cortex) 214 and triggers the release of Epinephrine (Epi), NE, and glucocorticoids into the blood stream, in particular cortisol 216 in humans. In general, the Epi/NE ratio released by the adrenals is 80/20.

Epi and NE primarily elicit a sympathetic response (e.g., increase heart rate). Cortisol 216 has various physiologic effects, including catecholamine release (e.g., Epi, NE, etc.), suppression of insulin, mobilization of energy stores through gluconeogenesis and glycogenolysis, as well as the suppression of the immune-inflammatory response. In addition, cortisol 216 serves as a feedback molecule-signal to limit the further release of CRH, thus slowing down the stress response.

The β-endorphins 210 are released from the pituitary gland 208 to opioid receptors primarily in the peripheral nervous system (but also to immune cells), where, amongst other effects, they produce analgesia. This analgesia is the result of a cascade of interactions resulting in inhibition of the release of tachykinins, particularly of substance P, which is involved in the transmission of pain.

The PVN 206 receives stress-related ascending monosynaptic afferent signals from several areas/nuclei. These nuclei include the Nucleus of the Solitary Track (NTS) 104, the LC 108, the parabrachial nuclei (PbN) 114, the Periaqueductal Grey Area (PAG) 110, and the Raphe Nucleus (RN) 106. These ascending pathways carry information regarding the stressor or stressors encountered. In addition to these ascending afferent signals, intrahypothalamic as well as descending afferent signals modulate the PVN 206 response to stressors. For example, signals from the Prefrontal cortex (PFC) 218, the Hippocampus (Hipp) 138, and the Amygdala 149 reach the PVN 206; in some cases, these signals are further integrated at the Bed Nucleus of the Stria Terminalis (BNST) before reaching the PVN 206. Together, these signals incorporate cognitive and memory information into the stress response.

Turning to FIG. 3A and FIG. 3B, psychological stressors are perceived and interpreted in an anticipatory fashion, and the response can be heavily modulated by the reward circuit, which includes the PFC 218, the Amygdala 149, the Ventral Tegmental Area (VTA) 306, as well as the Nucleus Accumbens (NAc) 126 (of FIG. 1A) (dopaminergic pathways, which are highly modulated by the central endorphin pathway 302). Under normal circumstances, the Pre-Limbic (PL) and Infra-Limbic (IL) areas of the PFC 218 coordinate a top-bottom control over the stress response to psychological stressors. However, under high stress levels or chronic stress scenarios this top-bottom control gets disrupted and a bottom-top control, heavily weighing the Amygdala's inputs, takes over the stress response to these psychological stressors. Having a bottom-top type response hinders the decision-making processes by not given proper weight to other signals; for example, to those afferent signals from the PFC 218 and the Hipp 138 (of FIG. 1A and FIGS. 2A and 2B).

The brain areas or nuclei forming the neural circuitry involved in the stress response are not only involved in depression but also are integral components of the Endogenous Opioid Circuit (EOC), which includes the Central Endorphin Pathway 302 (FIG. 3B) as well as the secondary connections arising from it. As illustrated in FIG. 3B, together with FIGS. 2A and 2B, the NTS 104, LC 108, PbN 114, PAG 110, RN 106, PFC 218, VTA 306, NAc 126 (as it receives afferents from the VTA 306), the Amygdala 149 are part of the EOC. The central endorphin pathway 302 interacts with several other brain regions or nuclei including with other hypothalamic areas such as the PVN 206. Stimulating afferent pathways to the central endorphin pathway 302 such as vagal and/or trigeminal structures activates this circuit and connected regions, including the VTA 306, which is one of the main producers of dopamine in the CNS. By activating the central endorphin pathway 302 and connected regions, systems and methods described herein are able to modulate stress and alertness levels.

As stated before, one of the characteristics of stress is a hyperactive SNS, and hypoactive PNS, or both; resulting in a high SNS/PNS activity ratio. An increase in the activity of the PNS leads to a faster return to baseline after a response to a stressor. One way to increase PNS activity is to increase vagal tone which can be achieved by increasing the activity of the Vagus nerve 156. Activation of The Main Parasympathetic Pathway 300 of FIG. 3A results in an increase in vagal tone and thus a better stress response. Amongst the main vagus nerve afferent pathways are those originating in the NTS 104, the NA 122, and the DMV 304 (of FIG. 3B). Activity in these regions generally results in an increase in vagal tone. Activation of the ABVN 118 and the ATN 130 directly and indirectly lead to increase activity in all three above mentioned pathways going from the NTS 104, the DMV 304, and the NA 122, to the Vagus nerve 156. As seen in FIG. 3A, these pathways also involve other nuclei or regions such as LC 108, PAG 110, RN 106, and TCC 102.

Figure 4B:
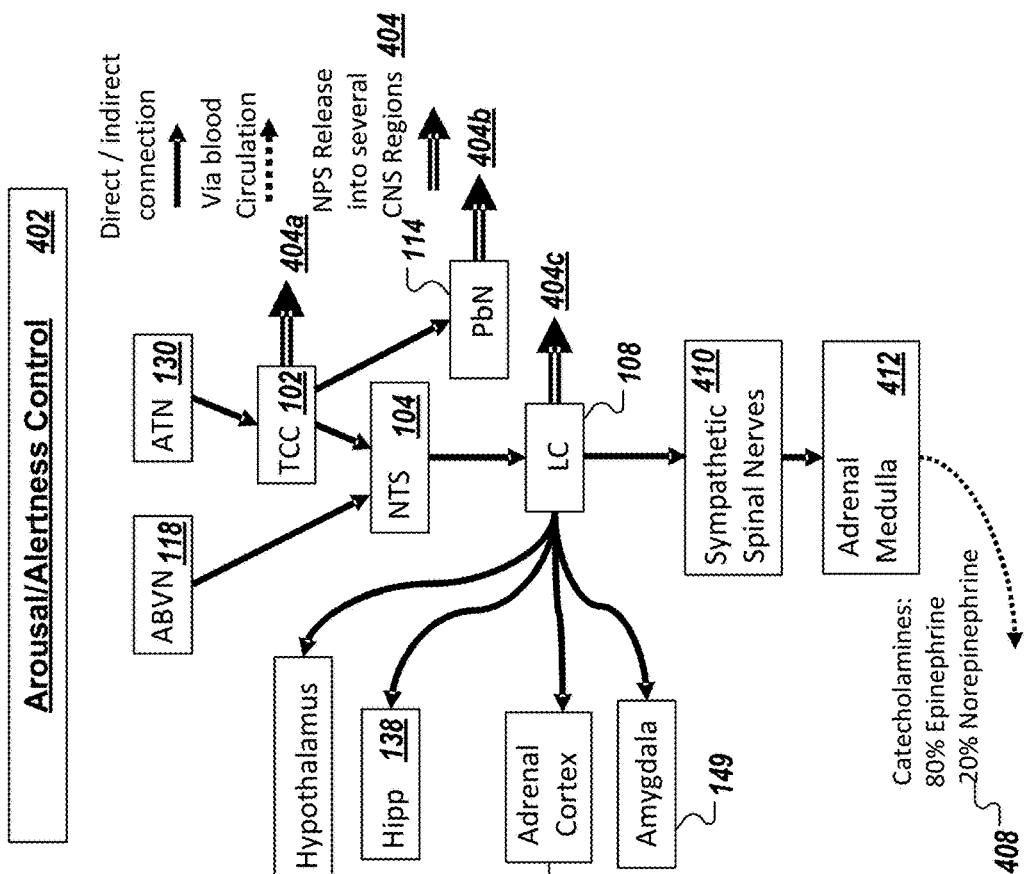
FIG. 4B illustrates example connections of an arousal and alertness control pathway.
Figure 4A:
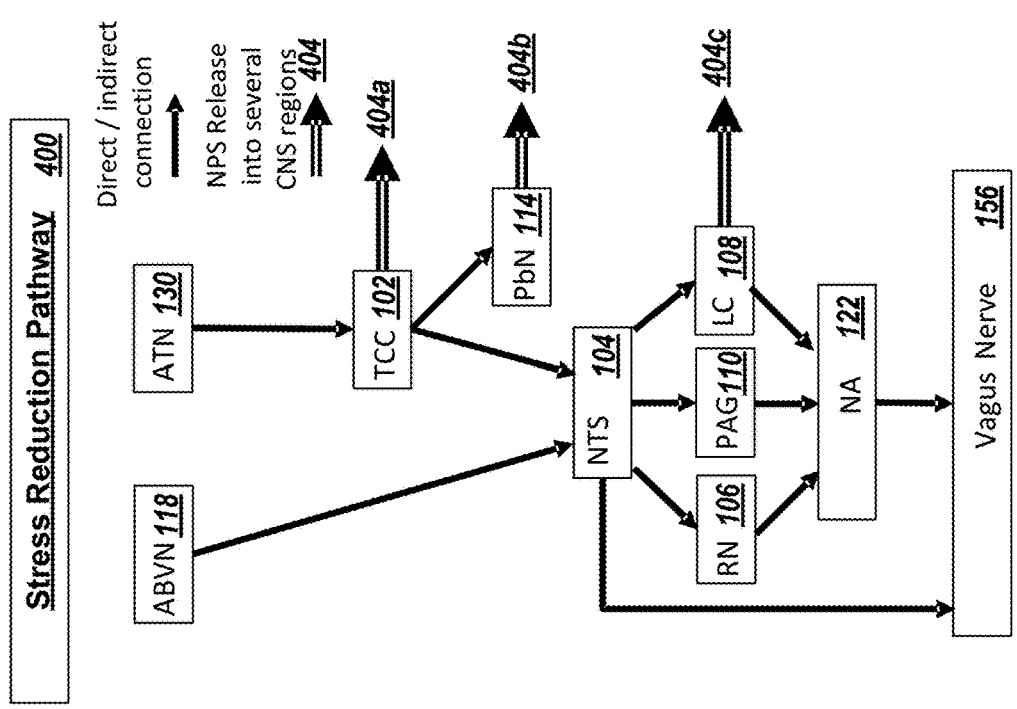
FIG. 4A illustrates example connections of a stress reduction pathway.

As can be seen from a comparison of the stress reduction pathway 400 of FIG. 4A with the main parasympathetic pathway 300 of FIG. 3A and the central endorphin pathway 302 of FIG. 3B, significant overlap exists. Turning to the stress reduction pathway 400 and arousal/alertness control pathway 402, stimulation (e.g., of the ABVN 118 and/or ATN 130) can be provided to trigger Neuropeptide S (NPS) release into several CNS regions 404. In the CNS, NE is primarily produced in the LC 108. NPS is produced in the LC 108, the trigeminal nucleus, and the Parabrachial Nucleus (PbN) 114. Neuropeptides as opposed to neurotransmitters require a higher level of activity to be released (e.g., higher frequency of neuronal activity at the production sites). The NPS release 404, for example, includes release via the TCC 102, the PbN 114, and the LC 108.

LC 108 activity is key for arousal. Both Norepinephrine 408 and NPS, which are produced in and around the LC 108, promote arousal and wakefulness. Thus, turning to FIG. 4B, interventions that increase NE and NPS in the CNS 404 also increase arousal, mitigating the effects of fatigue.

Descending pathways from the LC 108 directly activate sympathetic preganglionic neurons in the spinal cord (e.g., Coeruleo-Spinal Pathway). Activation of these sympathetic spinal neurons has a net sympathetic effect, such as for example an increase in heart rate. Many of the generalized sympathetic effects are a direct effect of the higher amount of circulating catecholamines, in particular epinephrine and norepinephrine. The main source of these catecholamines is the adrenal medulla 412, which is innervated by preganglionic sympathetic nerves 410. The adrenal medulla 412 releases a mix of approximately 80% epinephrine and 20% norepinephrine 408 into the blood stream when stimulated.

Heart rate variability (HRV) is a reflection of the state of the autonomic nervous system (ANS). The sympathetic branch of the ANS, which is more active during stress situations tends to increase heart rate (HR) and decrease HRV; the opposite is true for the parasympathetic branch of the ANS, which tend to decrease HR and increase HRV. Higher HRV has been associated with well-being and has been used as a health biomarker.

Figure 4C:
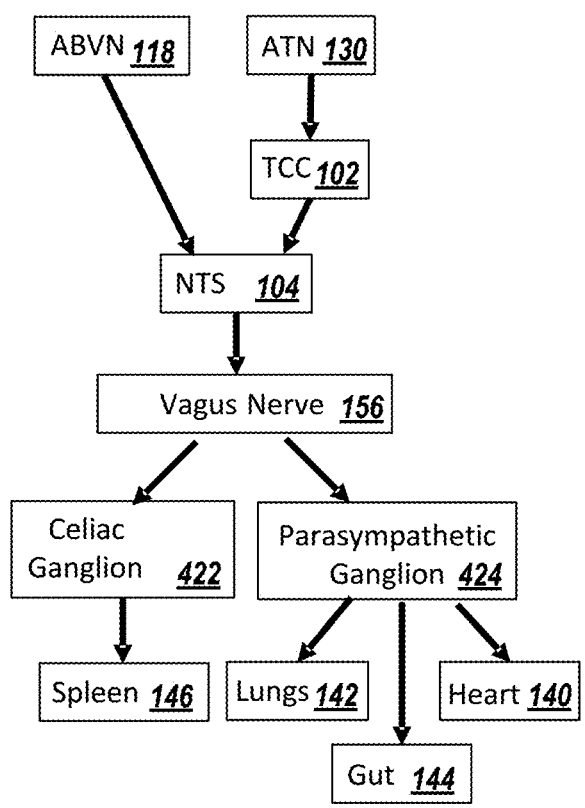
FIG. 4C illustrates example connections of an anti-inflammatory pathway.

In some implementations, an anti-inflammatory effect is provided via activation of an anti-inflammatory pathway 420 (e.g., the cholinergic anti-inflammatory pathway), as illustrated in FIG. 4C. In particular, the methods and devices described herein may activate the anti-inflammatory pathway by stimulating the ABVN 118 and/or the ATN 130 which, as stated before, have projections to the NTS 104. These projections elicit cholinergic anti-inflammatory effects via efferent pathways, mostly via the vagus nerve 156. Systemic anti-inflammatory effects occur when the vagus nerve 156 mediates spleen 146 function, thereby reducing the amount of circulating pro-inflammatory cytokines. In addition, a local anti-inflammatory effect occurs at organs reached by the efferent pathways; for example at the lungs 142, gut 144, and heart 140.

Decreasing systemic pro-inflammatory processes and/or pro-inflammatory processes in one or more target organs 140, 142, 144, and/or 146, in some implementations, involves modulating at least a portion of the anti-inflammatory pathway 420 such that activity at the NTS 104 is modulated affecting activity in efferent pathways through the celiac ganglion 422 and/or the parasympathetic ganglion 424, which in turn modulate activity in the spleen 146, lungs 142, gut 144, and/or heart 140 such that an anti-inflammatory response is elicited.

In some embodiments, the anti-inflammatory pathway 420 may be activated to reduce bleeding. For example, activation of a portion of the anti-inflammatory pathway 420, via stimulation of the vagus nerve 156, is discussed in U.S. Pat. No. 8,729,129 to Tracey et al., incorporated by reference herein in its entirety.

Figure 8A:
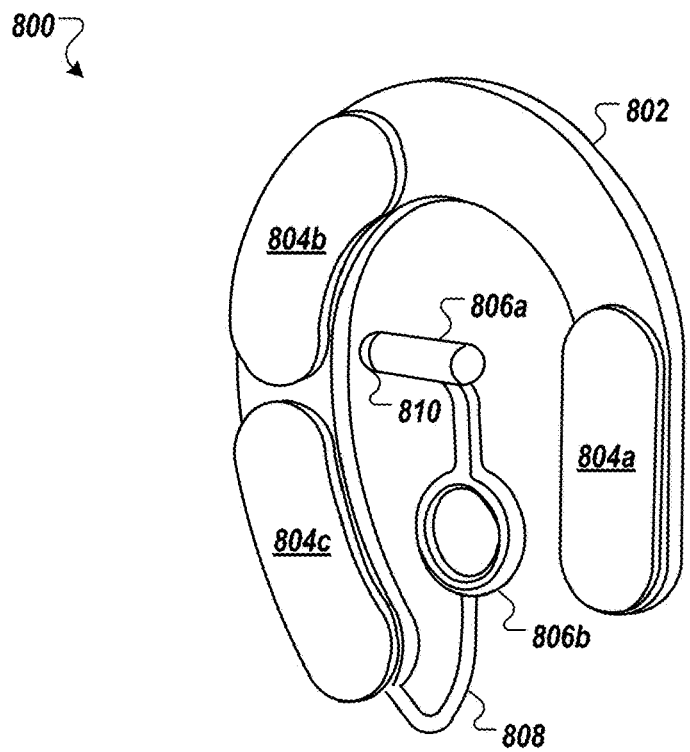
FIGS. 8A and 8B illustrate a first example auricular therapeutic device.
Figure 9A:
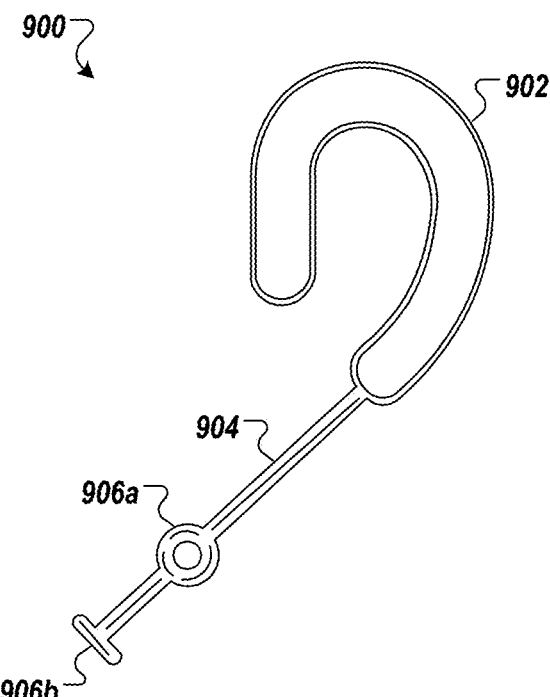
FIGS. 9A through 9C illustrate a second example auricular therapeutic device.

Turning to FIG. 5A, a stimulation flow diagram 500 illustrates stimulation mechanisms for controlling and/or decreasing stress 510 using a treatment device such as a treatment device 800 of FIG. 8A or a treatment device 900 of FIG. 9A. The stimulation mechanisms are produced by a first stimulation 502a and a second stimulation 502b. The first and second stimulations, in some embodiments, are temporally separated (e.g., in overlapping or non-overlapping stimulations). In some embodiments, the first and second stimulations are physically separated (e.g., using a different electrode or set of electrodes contacting a different location on the patient). The first and second stimulations, for example, may be provided via the stress reduction pathways 400 discussed in relation to FIG. 4A. According to the pathways 400, the first stimulation 502a and/or the second stimulation 502b may be configured to stimulate the ABVN 118 which projects to the prefrontal cortex and/or the ATN 130 which has a pathway to the prefrontal cortex 136 via the TCC 102.

Responsive to a first stimulation 502a, in some embodiments, parasympathetic activity and/or vagal tone is increased (504). For example, Enkephalins may increase BDNF mRNA expression in the hippocampus mediated by DOR and MOR mechanisms while β-Endorphin, endomorphin-1 and endomorphin-2 upregulate BDNF mRNA in the prefrontal cortex, hippocampus and amygdala. Production of dopamine (DA) in the Ventral Tegmental Area (VTA) 124 can be augmented by an increase in MOR agonist (e.g., endorphins and enkephalins); in particular by inhibiting GABAergic interneurons which in turn inhibit dopaminergic neurons in the VTA 124. Amongst other, these DAergic VTA neurons project to Nucleus Accumbens (NAc) 126, the Prefrontal Cortex (PFC) 136, the Hippocampus (Hipp) 138, and the Amygdala (Amyg) 149. These brain regions also share projections/connections amongst themselves making an important neuronal circuit known as the Reward Circuit or Reward Neural Circuit. Alterations leading to dysregulation, maladaptive regulation, or dysfunctional interactions in this neural circuit are seen in people with behaviors such as addiction, anxiety disorders including PTSD, and depression. Furthermore, a dysregulation in this circuit has also been observed in people showing behaviors associated with lower attention levels, for example in attention deficit disorder (ADD) and attention deficit hyper-activity deficit disorder (ADHD).

Further, in some implementations, the first stimulation 502a increases activity in one or more neural medullary structures 506a, such as the NTS 104, the spinal trigeminal nucleus, the NA 122, and at least some of the RN 106. The first stimulation 502a, for example, may increase 5-HT availability 506b, leading to an increase in BDNF expression. The BDNF, in turn, may function to protect monoamine neurotransmitter neurons and assist the monoamine neurotransmitter neurons to differentiate. In some embodiments, the second stimulation 502b also increases 5-HT availability 506b.

NPS is mainly produced in three areas in the brain: LC 108, PbN 404b, and the trigeminal nucleus, the latter being the target of the ATN 130 and at least partially included in the TCC 102. Activity in any of these three areas is necessary for NPS expression 404. In some implementations, the second stimulation 502b increases activity in neural structures in the TCC 508a. The second stimulation 502b, for example, may increases NPS release 508b via the activation cascade that follows the stimulation of the ATN 130.

In some embodiments, providing the first stimulation 502a and providing the second stimulation 502b involves providing a series of simultaneous and/or synchronized stimulation pulses. Each of the first stimulation 502a and the second stimulation 502b may be applied using the same or different parameters. The parameters, in some examples, may include pulse frequency (e.g., low, mid-range, or high) and/or pulse width. Further, the parameters may indicate electrode pairs for producing biphasic pulses. In a first illustrative example, the first stimulation may be applied using a low frequency, while the second stimulation is applied using a mid-range frequency. Conversely, in a second illustrative example, the first stimulation may be applied using a mid-range frequency, while the second stimulation is applied using a low frequency. Other combinations of low, mid-range, and high frequency stimulations are possible depending upon the patient and the disorder being treated. Therapy may be optimized according to the needs of individual patients including custom stimulation frequency, custom pulse width, custom stimulation intensity (amplitude), and/or independently controlled stimulation channels.

Turning to FIG. 5B, a stimulation flow diagram 520 illustrates stimulation mechanisms for promoting wakefulness and increasing arousal/alertness to counteract fatigue 528 using a treatment device such as a treatment device 800 of FIG. 8A or a treatment device 900 of FIG. 9A. The stimulation mechanisms are produced by a first stimulation 522a and a second stimulation 522b. The first and second stimulations, in some embodiments, are temporally separated (e.g., in overlapping or non-overlapping stimulations). In some embodiments, the first and second stimulations are physically separated (e.g., using a different electrode or set of electrodes contacting a different location on the patient). The first and second stimulations, for example, may be provided via the arousal alertness/control pathways 402 discussed in relation to FIG. 4B. According to the pathways 402, the first stimulation 522a and/or the second stimulation 522b may be configured to stimulate the ABVN 118 which projects to the prefrontal cortex 136 and/or the ATN 130 which has a pathway to the prefrontal cortex 136 via the TCC 102.

Responsive to a first stimulation 522a, in some embodiments, 5-HT and NE availability are increased (524), leading to an increase in BDNF expression. The BDNF, in turn, may function to protect monoamine neurotransmitter neurons and assist the monoamine neurotransmitter neurons to differentiate. In some embodiments, the second stimulation 522b also increases 5-HT and NE availability 524. NE and 5-HT are respectively produced in the Locus Coeruleus (LC) 108 and in the Raphe Nucleus (RN) 106. These brain regions are integral parts of the Endogenous Opioid Circuits (EOC). Activity in these brain regions (or brain areas) can be modulated by activating afferent pathways to the EOC such as some trigeminal and vagal branches.

Further demonstrating the previously mentioned link between the EOC, cognition, and depression, studies have shown that some antidepressants promote neurogenesis likely via the upregulation of Brain-Derived Neurotrophic-Factor (BDNF) in areas such as the hippocampus 138 and the prefrontal cortex (PFC) 136. BDNF plays a strong role in cognition, plasticity, neurogenesis, and neuronal survival. 5-HT has also been shown to have a role in such physiological activities. Furthermore, patients suffering from depression have been shown to have decreased plasma levels of BDNF, suggesting that depressive conditions would benefit from a therapy that could increase BDNF levels. Additionally, learning and memory as well as cortical plasticity is modulated by stimulation of vagal afferents through the synergetic action of ACh, 5-HT and BDNF. Further, acute vagal stimulation has been shown to increase NE and 5-HT release in the PFC 136 and the amygdala 149 as well as to enhance synaptic transmission in the hippocampus 138.

The cognitive improvement due to the increase in BDNF, which leads to a faster reorganization of neural circuits, can be leveraged not only to learn new things faster, but also to eliminate/extinguish undesirable and/or maladaptive behavior such as, in some examples, PTSD, phobias, and addictive behavior such as drug-seeking or overeating.

Also, it has been shown that vagal activation produces pairing-specific plasticity, thus stimulation of vagal afferents, irrespective of what neuromodulator is produced, can be used to eliminate and/or extinguish undesirable and/or maladaptive behavior such as those described above.

In another example, the cognitive enhancement provided by the systems and methods described herein can be used to overcome the cognitive problems that have been described to occur in people exposed to microgravity environments such as astronauts in the space station or on a long space travel such as visiting Mars.

Additionally, BDNF levels have been shown to have an inverse correlation with factors associated with cognitive decline and/or impediments, such as in Alzheimer's patients.

The second stimulation 522b, in some embodiments, increases NPS release 526. As discussed above, this increase in NPS production or expression is the result of the activation cascade that follows the stimulation of the ATN 130.

In some embodiments, providing the first stimulation 522a and providing the second stimulation 522b involves providing a series of simultaneous and/or synchronized stimulation pulses. Each of the first stimulation 522a and the second stimulation 522b may be applied using the same or different parameters. The parameters, in some examples, may include pulse frequency (e.g., low, mid-range, or high) and/or pulse width. Further, the parameters may indicate electrode pairs for producing biphasic pulses. In a first illustrative example, the first stimulation 522a may be applied using a low frequency, while the second stimulation 522b is applied using a mid-range frequency. Conversely, in a second illustrative example, the first stimulation 522a may be applied using a mid-range frequency, while the second stimulation 522b is applied using a low frequency. Other combinations of low, mid-range, and high frequency stimulations are possible depending upon the patient and the disorder being treated. Therapy may be optimized according to the needs of individual patients including custom stimulation frequency, custom pulse width, custom stimulation intensity (amplitude), and/or independently controlled stimulation channels.

Figure 5C:
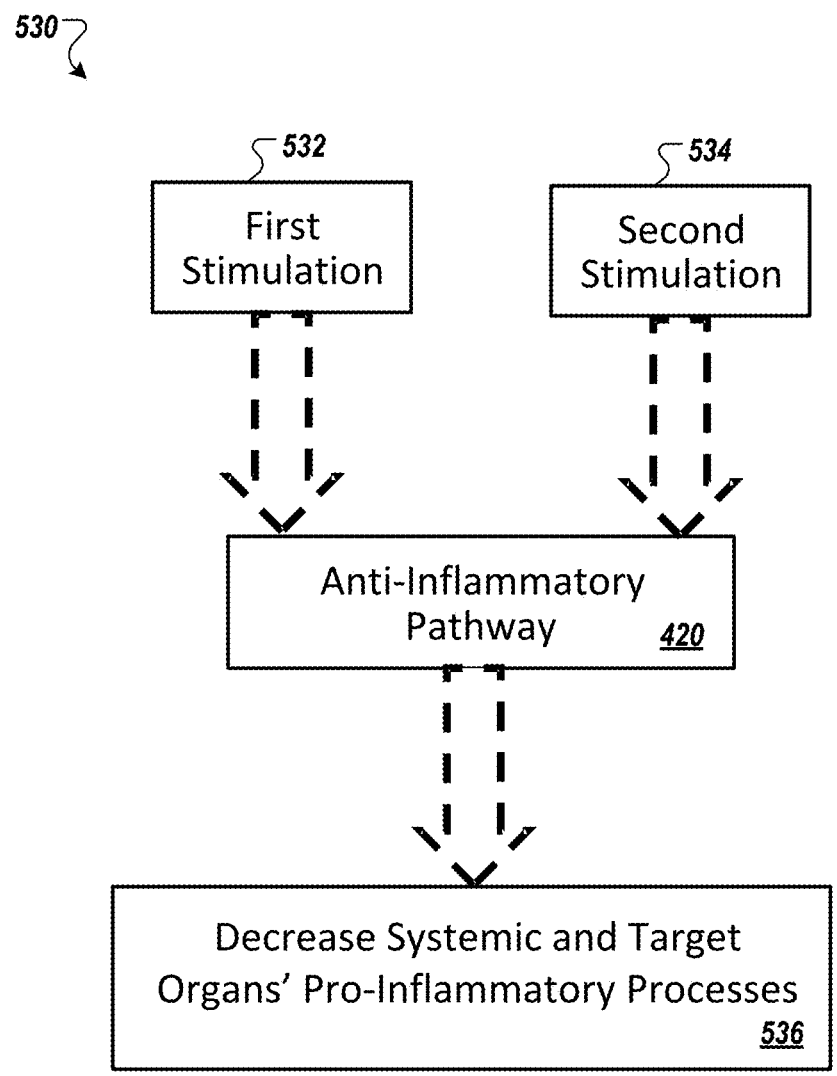
FIG. 5C illustrates example mechanisms for using electrical stimulation to decrease pro-inflammatory processes.

Turning to FIG. 5C, a stimulation flow diagram 530 is illustrated for providing therapy to decrease systemic pro-inflammatory processes and/or pro-inflammatory processes in one or more target organs. The target organs, for example, may include the spleen 146, lungs 142, gut 144, and heart 140. The stimulations of flow diagram 530, in some examples, may be applied in mitigating bleeding, reducing volume of bleeding, and/or reducing a time period of blood loss. The stimulations of flow diagram 530, for example, may be performed at least in part by a pulse generator.

In some implementations, a first stimulation 532 is provided at a first tissue location configured to stimulate the anti-inflammatory pathway 420 for decreasing systemic pro-inflammatory processes and/or pro-inflammatory processes in one or more target organs 536. The pathways, for example, may include a portion of the pathways illustrated in FIG. 4C. The first tissue location, for example, may include a surface of an ear structure contacted by an in-ear component of an auricular stimulation device. In some embodiments, the first stimulation 532 is supplied to multiple tissue locations. For example, the first stimulation 532 may be applied to a first tissue location including a surface of an ear structure contacted by an in-ear component of an auricular stimulation device as well as to a second tissue location on the tragus of the ear.

Decreasing systemic pro-inflammatory processes and/or pro-inflammatory processes in one or more target organs 536, in some implementations, involves modulating at least a portion of the anti-inflammatory pathway of FIG. 4C such that activity at the NTS 104 is modulated affecting activity in efferent pathways through the celiac ganglion 422 and/or the parasympathetic ganglion 424, which in turn modulate activity in the spleen 146, lungs 142, gut 144, and/or heart 140 such that an anti-inflammatory response is elicited.

In some implementations, a second stimulation 534 is provided at a second tissue location configured to stimulate the anti-inflammatory pathway 420 for decreasing systemic pro-inflammatory processes and/or pro-inflammatory processes in one or more target organs 536. Examples of target pathways and structures for stimulation of the second tissue location include those modulating activity at and/or on the auriculotemporal nerve 130, the lesser occipital nerve 152, and/or the great auricular nerve 154. The pathways, for example, may include a portion of the pathways illustrated in FIG. 5C.

In some embodiments, providing the first stimulation 532 and providing the second stimulation 534 involves providing a series of simultaneous and/or synchronized stimulation pulses to both the first tissue location and the second tissue location. Each of the first stimulation 532 and the second stimulation 534 may be applied using the same or different parameters. The parameters, in some examples, may include pulse frequency (e.g., low, mid-range, or high) or pulse width. Further, the parameters may indicate electrode pairs for producing biphasic pulses. In a first illustrative example, the first stimulation 532 may be applied using a low frequency, while the second stimulation 534 is applied using a mid-range frequency. Conversely, in a second illustrative example, the first stimulation 532 may be applied using a mid-range frequency, while the second stimulation 534 is applied using a low frequency. Other combinations of low, mid-range, and high frequency stimulations are possible depending upon the patient and the disorder being treated.

In other embodiments, the therapy provided by the first stimulation 532 and/or the second stimulation 534 of the stimulation flow diagram 530 includes automatically adjusting delivery of the therapy (e.g., adjusting one or more parameters) based on feedback received from the pulse generator or another computing device in communication with the pulse generator. The feedback, in some examples, may include a blood oxygen concentration, a breathing rate, a breathing variation, tidal volume, skin conductance, blood pressure, heart rate, heart rate variability, and/or EEG signal.

In further embodiments, combinations of the stimulations described in stimulation flow diagrams 500 and/or 520 with the stimulations described in stimulation flow diagram 530 may be used to enhance stress reduction through reducing the time and/or volume of the physical stressor of bleeding. Thus, activation of the anti-inflammatory pathway 420 in combination with activation of the stress reduction pathway 400 of FIG. 4A may mitigate stress reactions in subjects experiencing physical stress at least partially induced by bleeding. In a further example, in subjects performing stressful activities that have a substantial likelihood of resulting in bleeding (e.g., certain athletes, military personnel involved in active missions, etc.), activating the anti-inflammatory pathway 420 prior to initiation of bleeding may decrease or minimize bleeding if it occurs and may be used in combination with activation of the arousal/alertness control pathway 402 to improve performance, reduce tunnel vision, and maintain focus of the subject during the activity.

For example, the first stimulation 532 of the stimulation flow diagram 530 may be delivered synchronously or simultaneously with the second stimulation 502b of the stimulation flow diagram 500 of FIG. 5A for controlling and/or decreasing stress 510 or vice-versa. Similarly, for example, the first stimulation 532 of the stimulation flow diagram 530 may be delivered synchronously or simultaneously with the second stimulation 522b of the stimulation flow diagram 520 of FIG. 5B for promoting wakefulness, increasing arousal/alertness, and counteracting fatigue 528 or vice-versa. In another example, the therapy of the stimulation flow diagram 500, including both the first stimulation 502a and the second stimulation 502b may be delivered for a first period of time, and the therapy of the stimulation flow diagram 530, including both the first stimulation 532 and the second stimulation 534 may be delivered for a second period of time; or the therapy of the stimulation flow diagram 520, including both the first stimulation 522a and the second stimulation 522b may be delivered for a first period of time, and the therapy of the stimulation flow diagram 530, including both the first stimulation 532 and the second stimulation 534 may be delivered for a second period of time. The combined therapies, in some embodiments, may be repeated for a number of cycles of the first period of time and the second period of time. Based on feedback, the length of one or both of the first period of time and the second period of time may be adjusted to control/decrease stress 510 or promote wakefulness, increase arousal/alertness, and counteract fatigue 528 while decreasing systemic pro-inflammatory processes and/or pro-inflammatory processes in one or more target organs 536 in an efficient manner.

Figure 6A:
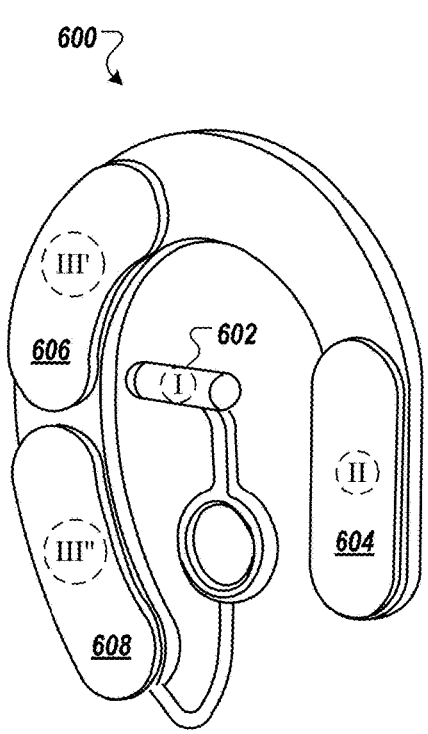
FIG. 6A and FIG. 6B illustrate an example electrode configuration and equivalent circuits for providing therapy.
Figure 6B:
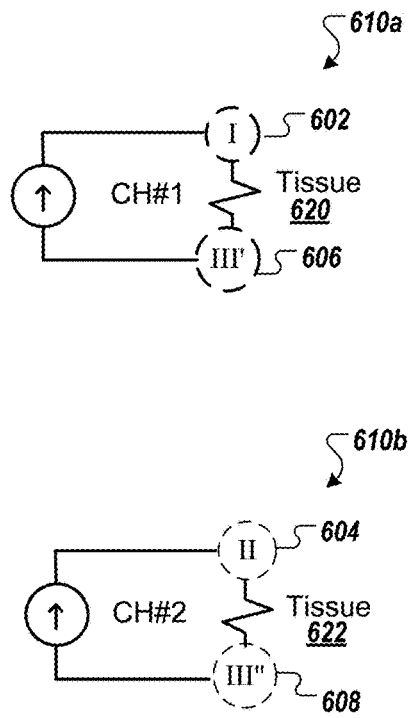

Turning to FIG. 6A and FIG. 6B, an example electrode configuration of an earpiece device 600 and example equivalent circuits 610a-b for providing therapy are shown. Turning to FIG. 6A, the earpiece device 600, in some implementations, includes inner ear component electrode 602, and auricular component electrodes 604, 606, and 608. Circuitry connecting between the electrodes 602, 604, 606, and 608 may be configured to form corresponding circuits 610a and 610b, as illustrated in FIG. 6B.

Turning to FIG. 6B, an equivalent circuit 610a is formed by electrode 602 and electrode 606 which are configured to stimulate tissue portions 620. In some implementations, the inner ear component electrode 602 is configured to contact a tissue portion 620 in the cymba conchae region which is enervated by branches of the auricular branch of the vagus nerve. The auricular component electrode 606, in some implementations, is configured to contact a tissue portion 620 in the region behind the ear which is enervated by branches of the great auricular nerve and/or branches of the lesser occipital nerve.

An equivalent circuit 610b is formed by electrode 604 and electrode 608 of the auricular component of the device 600 and configured to stimulate tissue portions 622. In some implementations, the tissue portions 622 are in the region rostral to the ear which is enervated by the auriculotemporal nerve as well as the region behind the ear which is enervated by branches of the great auricular nerve and branches of the lesser occipital nerve.

In further implementations, the tissue portions include the concha which may be stimulated, for example, at approximately 5 Hz or at approximately 15 Hz. In other implementations, the tissue portions include tissue enervated by the trigeminal nerve which may be stimulated, for example, at approximately 100 Hz.

Figure 7:
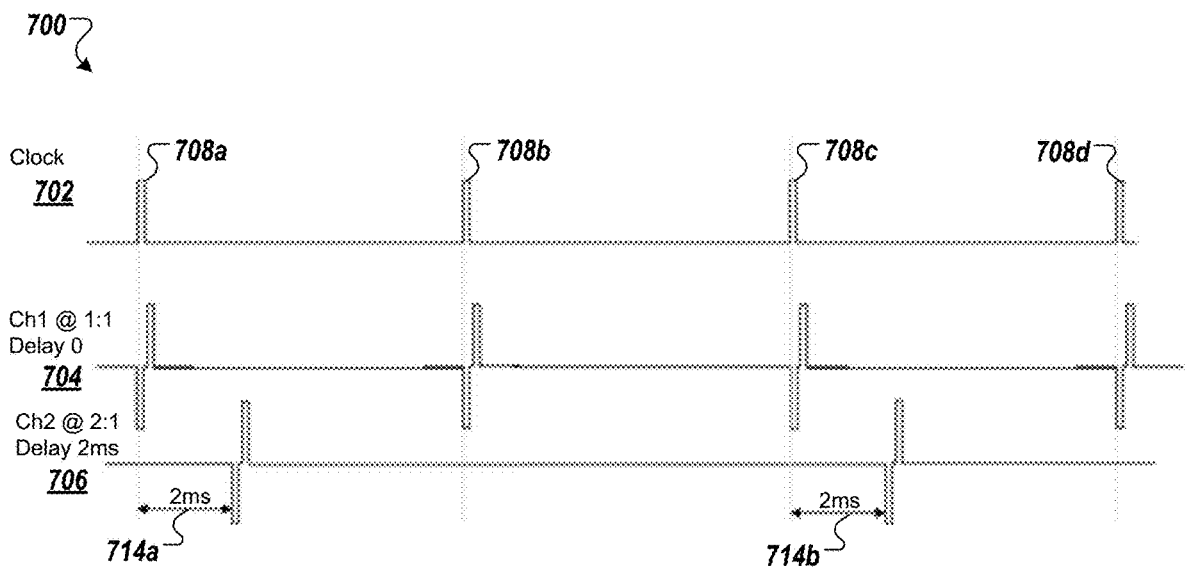
FIG. 7 illustrates an example timing diagram for supplying stimulation pulses to an auricular therapeutic device.

In some embodiments, the equivalent circuit 610a is stimulated by a first channel and equivalent circuit 610b is stimulated by a second channel. FIG. 7 pictures a timing diagram 700 illustrating the triggering of multiple channels 704 and 706 using a master clock 702 according to an example. In some embodiments, the clock 702 triggers pulses 708 at a predetermined clock frequency. In an example, a first channel 704 can be configured to trigger stimulation of equivalent circuit 610a and a second channel 706 can be configured to trigger stimulation of equivalent circuit 610b of FIG. 6B. Conversely, the triggering can be reversed, for example, where equivalent circuit 610b is triggered before equivalent circuit 610a.

In some implementations, stimulation is configured to be triggered by every pulse of the master clock 702; i.e., at a 1-to-1 ratio. In some embodiments, stimulation by one channel 704, 706 is configured to be triggered following a specific time interval after the pulse triggered by the other channel 704, 706 ends. In some embodiments, one of the channels 704, 706 is be configured to be triggered based on every other pulse of the master clock; i.e., at a 2-to-1 ratio with the master clock. For example, the triggering by the second channel 706, as shown occurs every other clock cycle and after a specific time delay 714 from the master clock pulse 708. In other embodiments, stimulation by the second channel 706 may be configured to be triggered following a specific time interval after the pulse triggered by the first channel 704 ends. In some embodiments, stimulation from one channel 704, 706 is offset from stimulation by the other channel 704, 706 by a synchronous delay. As illustrated, the synchronous delay 714 is 2 ms and can be as little as zero (making both channels to trigger simultaneously depending on the master clock ratio for each channel) and as much as the master clock period less the combined duration of the stimulations provided by channel 704 and 706 plus the time interval between them. In some embodiments, this delay can be about 10 ms.

In some implementations, the equivalent circuits 610a, 610b are synchronized using a master clock counter and a register per channel. By setting each register to a number of master clock pulses to trigger the respective channel, each channel may be configured to be triggered when the channel register value equals the master clock pulses. Subsequently, the counter for each channel may be reset after the channel is triggered. In an example, using a 6-bit counter and a 6-bit register, the trigger frequency can be as high as the master clock frequency (1:1) and as low as 1/64 of the clock frequency (64:1).

Stimulation delivery may vary based upon the therapy provided by the treatment device. Frequency and/or pulse width parameters, for example, may be adjusted for one or more if not all electrodes delivering stimulation. In some embodiments, frequency and/or pulse width parameters are adjusted during therapy, for example responsive to feedback received from monitoring the patient (e.g., using one or more sensors or other devices). The stimulation frequencies, in some examples, may include a first or low frequency within a range of about 1 to 30 Hz, a second or mid-range frequency within a range of about 30 to 70 Hz, and/or a third or high frequency within a range of about 70 to 150 Hz. Stimulation pulses, in some embodiments, are delivered in patterns. Individual pulses in the pattern may vary in frequency and/or pulse width. Patterns may be repeated in stimulation cycles.

In one embodiment, the stimulation patterns are such that stimulating frequencies are not the same in all electrodes. In one embodiment, a stimulation frequency is varied between 2 Hz and 100 Hz such that different endogenously produced opioid receptor agonist are released (e.g., Mu, Delta, Kappa, nociception opioid receptor agonist). In yet another embodiment, the pulse width can be adjusted from between 20 and 1000 microseconds to further allow therapy customization.

In some embodiments, different stimulation frequencies are used at the different electrodes. In illustration, different combinations of high, mid-range and low frequencies can be used at a cymba electrode (602), an auriculotemporal electrode (604), and/or a great auricular nerve and lesser occipital nerve electrode (606, 608). For example, a first or low frequency of between 1 to 30 Hz, or in particular one or more of 1 to 5 Hz, 5 to 10 Hz, 10 to 15 Hz, 15 to 20 Hz, 20 to 25 Hz, 25 to 30 Hz may be used at an in-ear electrode, while a second of high frequency of between 70 and 150 Hz, or in particular one or more of 70 to 75 Hz, 75 to 80 Hz, 80 to 85 Hz, 85 to 90 Hz, 90 to 95 Hz, 95 to 100 Hz, 100 to 105 Hz, 105 to 110 Hz, 110 to 115 Hz, 115 to 120 Hz, 120 to 125 Hz, 125 to 130 Hz, 130 to 135 Hz, 135 to 140 Hz, 140 to 145 Hz, 145 to 150 Hz is used at tissue surrounding the ear, such as an auriculotemporal electrode. In another example, a third or mid-range frequency of between 30 to 70 Hz, or in particular one or more of 30 to 35 Hz, 35 to 40 Hz, 40 to 45 Hz, 45 to 50 Hz, 50 to 55 Hz, or 55 to 60 Hz or 60 to 65 Hz or 65 to 70 Hz can be used at one or more of the electrodes. In yet another example, one or more low or mid-range frequencies can be used at an in-ear electrode such as the cymba electrode 602, while one or more high frequencies is used at an electrode contacting tissue surrounding the ear, such as the auriculotemporal electrode 604. In another example, a high frequency can be use at an in-ear electrode such as the cymba electrode 602 while a low frequency can be used at an electrode contacting tissue surrounding the ear, such as the auriculotemporal electrode 604.

Different combinations of pulse widths can be used at each electrode. Pulse widths, in some examples, may range from one or more of the following: first or short pulse widths within a range of about 10 to 50 microseconds, or more particularly between 10 to 20 microseconds, 20 to 30 microseconds, 30 to 40 microseconds, 40 to 50 microseconds; second or low mid-range pulse widths within a range of about 50 to 250 microseconds, or more particularly between 50 to 70 microseconds, 70 to 90 microseconds, 90 to 110 microseconds, 110 to 130 microseconds, 130 to 150 microseconds, 150 to 170 microseconds, 170 to 190 microseconds, 190 to 210 microseconds, 210 to 230 microseconds, or 230 to 250 microseconds; third or high mid-range pulse widths within a range of about 250 to 550 microseconds, or more particularly between 250 to 270 microseconds, 270 to 290 microseconds, 290 to 310 microseconds, 310 to 330 microseconds, 330 to 350 microseconds, 350 to 370 microseconds, 370 to 390 microseconds, 390 to 410 microseconds, 410 to 430 microseconds, 430 to 450 microseconds, 450 to 470 microseconds, 470 to 490 microseconds, 490 to 510 microseconds, 510 to 530 microseconds, or 530 to 550 microseconds; and/or fourth or long pulse widths within a range of about 550 to 1000 microseconds, or more particularly between 550 to 600 microseconds, 600 to 650 microseconds, 650 to 700 microseconds, 700 to 750 microseconds, 750 to 800 microseconds, 800 to 850 microseconds, 850 to 900 microseconds, 900 to 950 microseconds, or 950 to 1000 microseconds. Different embodiments can use different ranges of pulse widths at one or more of the electrodes (e.g., the electrodes 602, 604, 606, 608).

In yet another embodiment, a variable frequency (i.e., stimulating a non-constant frequency) can be used at one or more of the electrodes (e.g., 602, 604, 606, 608). The variable frequency can be a sweep, and/or a random/pseudo-random frequency variability around a central frequency (e.g., 5 Hz+/−1.5 Hz, or 100 Hz+/−10 Hz).

Figure 8B:
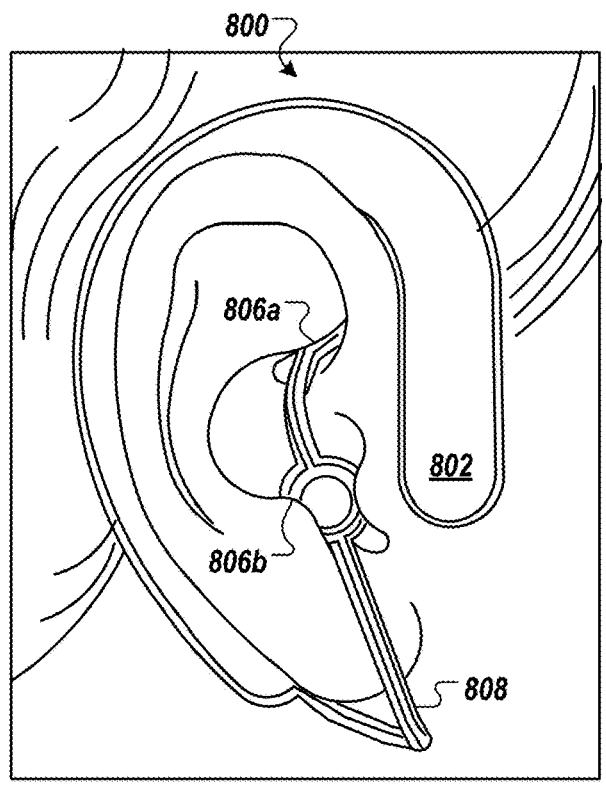

To stimulate the various neural structures discussed above, in some implementations, treatment devices may be designed for positioning against various surfaces on or surrounding a patient's ear. Turning to FIGS. 8A and 8B, an example treatment device 800 is shown including an auricular component 802 configured to contact skin behind and around a patient's ear. The auricular component 802, for example, may wrap around a back of an ear and include electrodes 804 for contacting skin surfaces in front of and behind the ear. The auricular component 802 is connected to an inner ear component 806 by a connector 808.

The connector 808, in some embodiments, is releasably connected between the auricular component 802 and the inner ear component 806. For example, at least one of a proximal (auricular component 802 side) end or at distal (inner ear component 806) end of the connector 808 may be designed for releasable connection. In other embodiments, the connector 808 is integrated with the auricular component 802 and inner ear component 806, behaving as a conduit for bridging an electrical connection between the auricular component 802 and the inner ear component 806.

In some implementations, the auricular component 802 includes a number of electrodes 804 that are configured to be in contact with the dermis on and around the outer ear. The auricular component 802, in some examples, may include an electrode positioned for proximity to vagal-related neural structures, an electrode positioned for proximity to a neural structure related to the auriculotemporal nerve, an electrode positioned for proximity to neural structures related to the great auricular nerve or its branches, and/or an electrode positioned for proximity to the lesser occipital nerve or its branches.

Additionally, the treatment device 800 includes a pulse generator or controller (not illustrated) for delivering a series of therapeutic electrodes to the treatment device 800. The pulse generator may include management software for controlling therapy delivery. The management software, in some examples, may include adjustment functionality for customizing the therapeutic output, input/output (I/O) functionality (e.g., for confirmation of therapeutic delivery), and/or metrics collection functionality for generating and retaining data such as stimulation logs, diagnostic data, and/or event data.

In some embodiments, the controller records overall therapeutic delivery so the caregiver/clinician can measure compliance. In one example, the management software may notify the wearer, caregiver, clinician if the device has stopped delivering therapy. In a further example, the device 800 may provide an indication of health status, such as reporting on the condition of the electrodes, the conductive hydrogel, and/or the analgesic. In another example, the management software may report data related to use, events, logs, errors, and device health status. The controller, for example, may collect information for presentation in usage reports (e.g., generated by a separate portable device app or computer program). In some implementations, the treatment device 800 includes a unique identifier that can be used in identifying users and reported data so that multiple devices can be monitored using a single software application (e.g., patients at a certain facility and/or under supervision of a certain doctor).

In some embodiments, a pulse generator is connected to the auricular component 802 by a second connector. The second connector may be releasably connected between the auricular component 802 and the pulse generator. For example, at least one of a proximal (auricular component 802) end or a distal (pulse generator) end of the second connector may be designed for releasable connection. In other embodiments, the second connector is integrated with the auricular component 802 and the pulse generator, behaving as a conduit for bridging an electrical connection between the auricular component 802 and the pulse generator. In further embodiments, a pulse generator is built into the auricular component 802.

The first connector 808 and/or the second connector, in some embodiments, includes a keyed releasable connection with a corresponding port of the treatment device 800 for snug (e.g., non-spinning) connection or for assuring electrical alignment. In some embodiments, the first connector 808 and/or the second connector is designed for locking connection with the treatment device 800. The locking connection, for example, may be a water-resistant locking connection to protect against shorting due to moisture from sweat, rain, etc.

In some embodiments, the auricular component 802 and/or the inner ear component 806 are designed from inexpensive materials, allowing the apparatus to be disposable, thereby lowering the cost per treatment and eliminating the need for maintenance. Disposable apparatus also provides for greater hygienics.

In an illustrative example, a treatment device such as the device 800 of FIGS. 8A and 8B may be donned as follows. In implementations having protective liners on the skin adhesive and/or electrodes, remove the protective liners before use. Apply the auricular component 802 around the auricle of the patient and press against the patient's skin such that exposed skin adhesives and adhesives/hydrogels adhere to the skin. Next, place the inner ear component 806 in the ear such that a first portion 806b of the inner ear component 806 is positioned outside the external ear canal in the cavum. Finally, flex or compress a second or distal portion 806a of the inner ear component 806 supporting a cymba electrode 810 until it engages with the cymba of the ear.

Electrodes can be made larger or combined such that, for example, multiple electrodes are combined into one large contact, such as the contact pads 804a, 804b, and 804c. A treatment device, in some embodiments, includes a set of electrodes configured to be virtually grouped together to form one or more effective electrodes. For example, a first grouping of electrodes can be equivalent to electrode 804a, a second grouping of electrodes can be equivalent to electrode 804b, and a third grouping of electrodes can be equivalent to electrode 804c. Grouping smaller electrodes provides the ability to have multiple electrodes each with its own independently controlled current source, allowing for current steering, thereby providing better spatial resolution and targeting capabilities. Electrodes may be virtually grouped by processing circuitry.

In some implementations, a treatment device includes one or more haptic feedback actuators between electrode pairs. The haptic feedback actuator(s), for example, may move from a first position to a second position in repetitive patterns to mask sensations felt by stimulation of the electrodes. The haptic feedback actuator(s) may be configured to isolate or electrically separate conductive shunting pathways between electrodes, for example between portions of conductive gel.

Figure 9B:
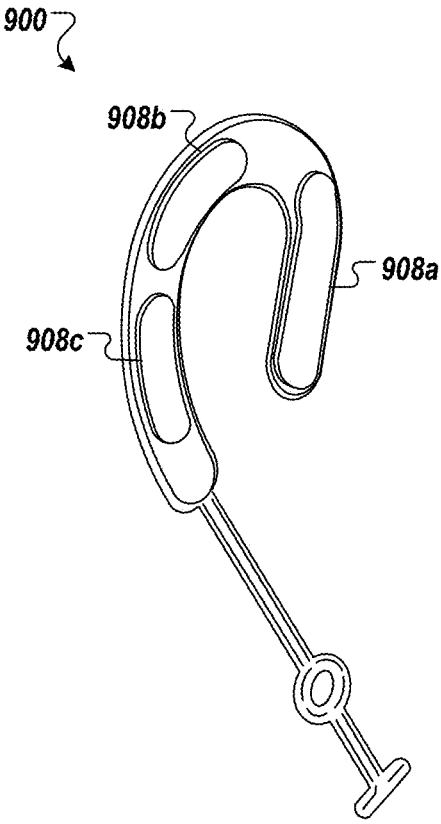
Figure 9C:
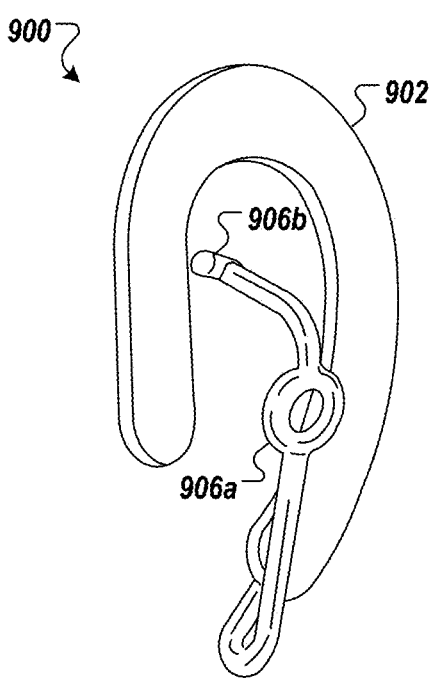

Turning to FIG. 9A through FIG. 9C, in some implementations, an earpiece assembly 900 includes a printed circuit board (PCB) layer having electrodes. A flexible PCB can include electronic components to suppress electrical spikes as well as a component to identify and/or uniquely identify the PCB. Exposed conductive surfaces on the PCB can serve as contact point to connect hydrogels to the PCB. The PCB extends forming a cable-like structure (connector) 904 to integrate an inner ear component 906 and an auricular component 902 without the need for soldering and/or connecting during assembly. The earpiece assembly 900, in some embodiments, is extremely flexible, allowing it to easily conform to different shapes presented by the anatomic variability of users. In some embodiments, the earpiece assembly 900 is at least partially custom printed to provide a fitted shape for the user.

In some implementations, the flexible PCB is encapsulated in a protective covering. The protective covering can be made from a flexible material such as silicone. The protective covering may be applied in varying thickness and/or densities, for example to improve comfort during wear, to increase retention strength of the device during wear, and to protect the circuitry from damage. The encapsulation is done with at least one material. In some embodiments, the encapsulation is done at least in using one mold and at least one molding step. The flexible PCB, for example, may be at least partially covered with a closed cell foam.

Turning to FIG. 9B, in some implementations, the auricular component 902 includes a set of electrode contacts 908a, 908b, and 908c. More or fewer electrode contacts may be included, and each electrode contact may be in electrical contact with one or more electrodes of the PCB layer. The protective covering, in some implementations, includes openings to expose contacts to electrodes. For example, electrode contact pads 908a-c may be added to exposed regions. In other implementations, the entire earpiece assembly 900 is printed, including the protective layer and the contact pads 908a-c.

In some embodiments, the skin-contacting electrodes of the earpiece assembly 900 are formed in layers. For example, a first layer may include a medical-grade double-sided conducting adhesive tape, the second layer may include a conductive flexible metallic and/or fabric mesh for mechanical robustness and homogenic electrical field distribution, and a third layer may include a self-adhesive hydrogel. In other embodiments, a two-layer version may be provided having a first layer configured for mechanical robustness and homogenic electrical field distribution and a second layer including a self-adhesive hydrogel. The PCB electrodes may be formed such that they cover a similar surface area as the skin-contacting hydrogel electrodes. In this manner, homogenic electrical field distribution may be achieved at the hydrogels without the need of any additional conductive layer.

In some implementations, a first portion 906a of the inner ear component 906 and/or a second portion 906b of the inner ear component 906 includes one or more stimulation electrodes. The electrodes may be exposed (e.g., no protective layer covering) and/or one or more contact pads may be applied to the first portion 906a and/or the second portion 906b.

The connector 904, in some implementations, is designed to curve up to allow for insertion of the inner ear component 906, as illustrated in FIG. 9C. In other implementations, the connector 904 is printed as a spring (e.g., telephone cord) to provide mobility of the inner ear component 906.

In some implementations, the earpiece assembly 900 connects to a pulse generator via a slim keyed connector. In other implementations, the PCB layer includes controller circuitry for generating pulses.

In some implementations, a pulse generator for use with an earpiece device includes a battery and circuitry configured to produce therapy stimulation in communication with the electrodes of the earpiece device. In some embodiments, the pulse generator includes at least one antenna configured to receive programming instructions encoding stimulation parameters. The system may be rechargeable to allow for long-term use.

In some embodiments, the auricular component 902 of the earpiece device is connected to an electrical pulse generator which produces the therapy stimulation going to the electrodes 908 on the auricular component 902 and the inner ear component 906. In some implementations, the pulse generator is located in close proximity with the auricle of the patient. For example, the pulse generator may be designed into or releasably connected to a head apparatus similar an over the head or back of the head headphones band or earmuffs band. In another example, the pulse generator may be releasably retained in a pocket of a cap or head wrap donned by a patient. In other embodiments, the pulse generator is placed on the body of the user, for example on the pectoral region just below the clavicle. In another embodiment, the pulse generator can be clipped to the user's clothing or carried in the user's trousers pocket or in a specially designed pouch. In further embodiments, the pulse generator is built into the auricular component 902 of the earpiece device.

In some embodiments, the pulse generator includes an input/output (I/O) interface for user control of the therapy. The I/O interface, for example, may include a number of controls, such as buttons, dials, or a touch pad, for adjusting therapy. In some examples, the I/O interface may include one or more of a mode selection, a length of time selection, or a stimulation strength control. Separate controls, in a further example, may be provided for the adjustment of the electrodes of the concha apparatus and for the electrodes of the earpiece.

In some embodiments, the pulse generator is remotely configurable via wireless communication. In some embodiments, the wireless remote device may periodically request therapy status and in some embodiments the status, including any changes, may be communicated to a 3rd party such as a healthcare provider who is monitoring the therapy being applied to the user. For example, therapy provided via the pulse generator may be controlled or adjusted at least in part using a peripheral device such as a mobile device, a tablet, or a personal computer. For example, a mode and/or stimulation strength may be adjusted by a clinical user (e.g., doctor, nurse, occupational therapist, etc.), while the timing (e.g., powering on and off and/or length of time setting) of the stimulation may be user-controlled via the I/O interface of the pulse generator. In another example, a software update to the pulse generator may be delivered via wireless communication. The wireless communication, in some examples, can include radio frequency (RF) communication (e.g., Bluetooth) or near-field communication (NFC). The wireless communication may be enabled via an application installed on the peripheral device.

In some embodiments, other components of the treatment device are configurable by or capable of communication with a peripheral device. For example, data collected by the treatment device may be transferred to the peripheral device and thereby exchanged via a computing cloud with third parties such as healthcare professionals and/or healthcare providers.

In some implementations, a therapeutic auricular device is designed for continuous use for, in some examples, at least thirty minutes, between a half hour and an hour, between one hour and five hours, or for a complete workday (e.g., approximately 8 to 10 hours). However, a device designed for continuous use can be utilized intermittently for short time intervals, or specific duty cycles. For example a device could be active for one 5-to-10 minute period or for several of such periods with an off time between the active periods. For example, for military training and/or operations, soldiers may be provided with continuous or intermittent therapy for a number of hours. A power pack, for example, may be tethered to the therapeutic auricular device and attached to/integrated into a variety of standard equipment, such as a military helmet or air traffic controller headset, to provide adequate power for longer term use. The power pack may include additional circuitry, such as controller circuitry for delivering stimulations.

In some implementations, control circuitry and/or a power unit may be releasably attachable to a therapeutic auricular device. For example, a controller component may snap onto or otherwise engage with the auricular component of a therapeutic auricular device to provide stimulation therapy. The therapeutic auricular device may be disposable, and the releasable control circuitry and/or power unit may be reusable.

A therapeutic auricular device, in some implementations, is designed for durability and retention throughout strenuous activities such as, in some examples, military training and/or military operations, police operations, and/or sports competitions (including e-sports). The therapeutic auricular device, for example, may include water resistance features, impact resistance features, adhesive features and/or anti-slippage features.

In some embodiments, a therapeutic auricular device includes few or no inputs accessible to the wearer. For example, the therapeutic auricular device may include a power control button or switch. A disposable therapeutic auricular device may include a removable battery tab that, when removed, engages power to the device and initiates therapeutic delivery.

In some embodiments, a therapeutic auricular device includes circuitry and/or other components to integrate the therapeutic auricular device with other devices, such as communications devices. For example, the therapeutic auricular device may include a wireless speaker component, wireless signal reception, and/or wireless signal transmission. A therapeutic auricular device may include a Bluetooth or other limited range wireless communication module for remote therapy initiation. In an illustrative example, upon the beginning of a mission or military operation, the therapeutic auricular devices of a group of individuals (e.g., military battalion, special weapons and tactics (SWAT) team, etc.) may be triggered to initiate therapy via a wireless command or signal issued by a single master controller. The signal may be a radio frequency (RF) signal issued to a passive or active RF component of the therapeutic auricular device.

Figure 10A:
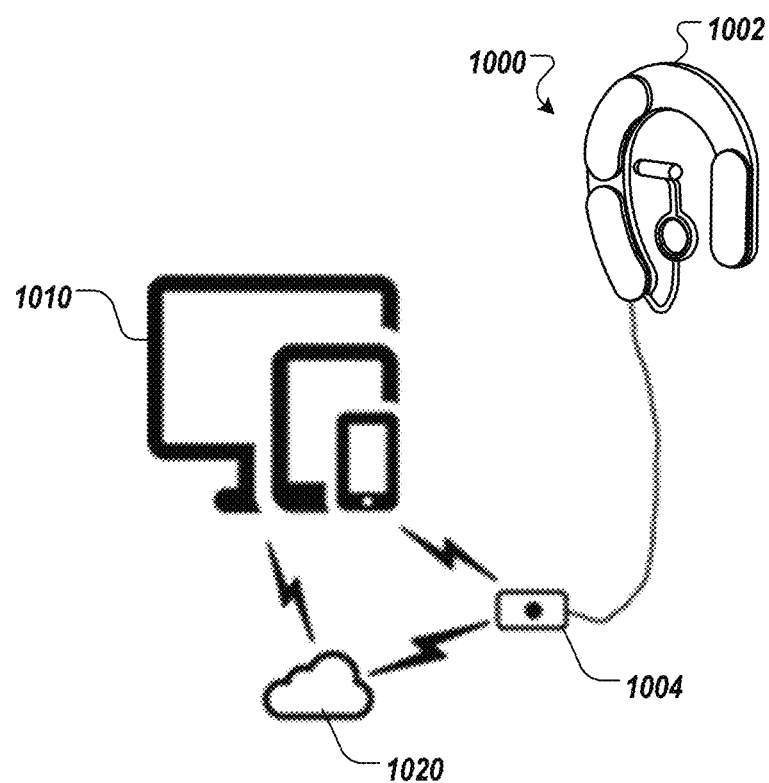
FIGS. 10A through 10C are drawings of example systems including an example treatment device in communication with remote systems through a computing cloud and/or a peripheral device.
Figure 10B:
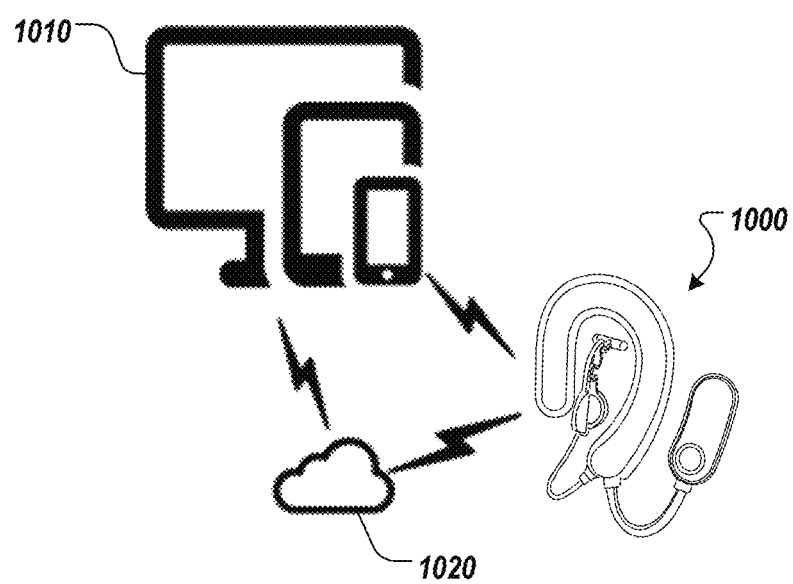
Figure 10C:
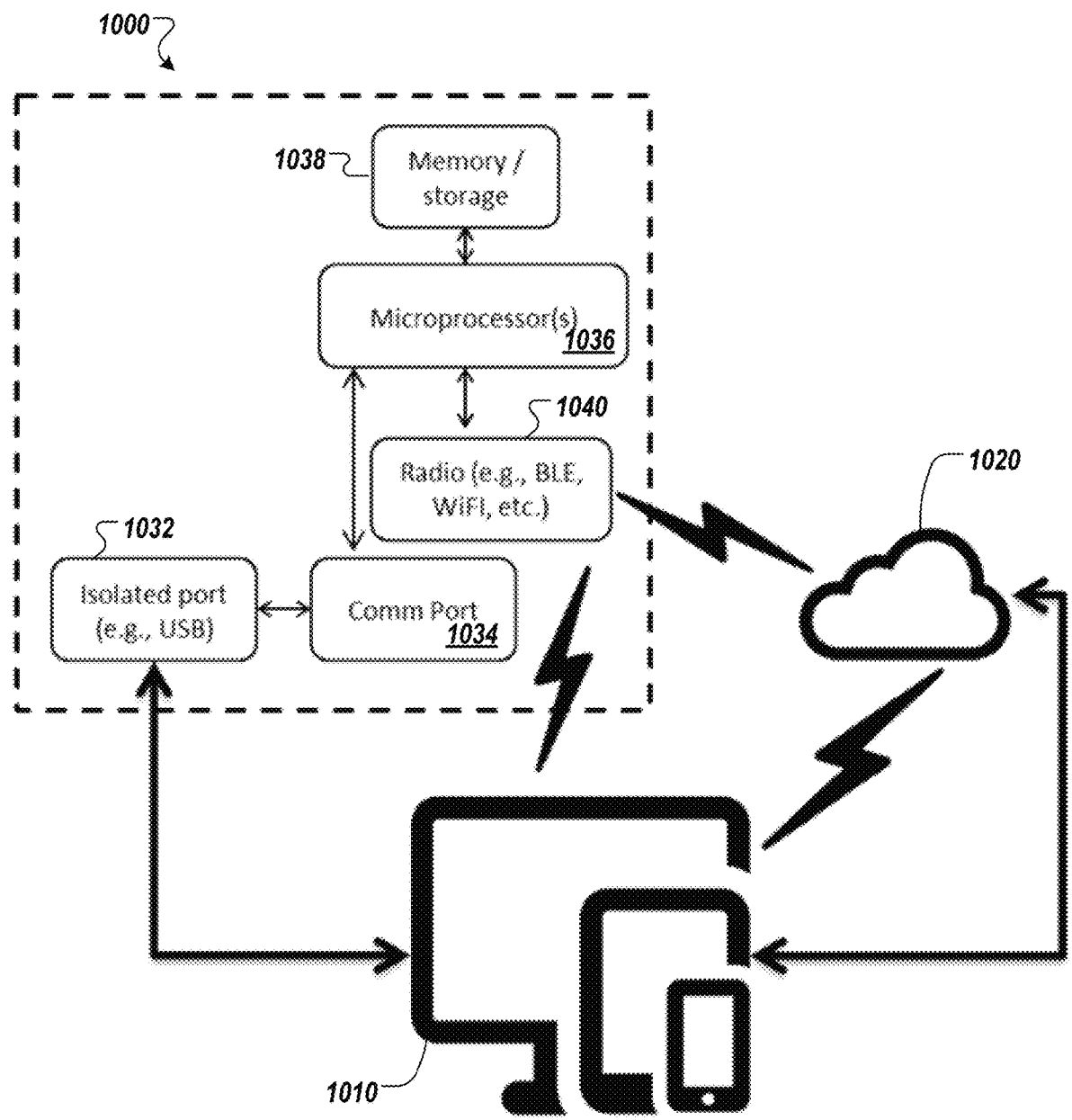

Turning to FIG. 10A through FIG. 10C, in some implementations, a treatment system can include a treatment device 1000 in communication with a network 1020 and/or one or more peripheral devices 1010. Certain peripheral devices 1010, further, may enable communication between the treatment device 1000 and one or more third parties. Examples of peripheral devices 1010 include a personal computer, a tablet, or phone. In some embodiments, the peripheral device(s) 1010 include a fitness-monitoring device, such as a Fitbit, Apple Watch, or Garmin Smartwatch. In some embodiments, the peripheral device (s) 1010 include a health-monitoring device, such as a glucose meter, a holter monitor, an electrocardiogram (EKG) monitor, or an electroencephalogram (EEG) monitor. Further, the peripheral devices 1010, in some embodiments, include a remote server, server farm, or cloud service accessible via the network 1020. Certain peripheral device(s) 1010 may communicate directly with the treatment device 1000 using short-range wireless communications, such as a radio frequency (RF) (e.g., Bluetooth, Wi-Fi, Zigbee, etc.) or near-field communication (NFC). Certain peripheral device(s) 1010 may communicate with the treatment device 1000 through another peripheral device 1010. For example, using Bluetooth communications, information from the treatment device 1000 may be forwarded to a cloud service via the network 1020 (e.g., using a Wi-Fi, Ethernet, or cellular connection). The network 1020, in some examples, can include a local area network (LAN), wide area network (WAN), metro area network (MAN) or the Internet. In some embodiments, the network is a clinical LAN used for communicating information in a medical environment, such as a hospital, in a secure (e.g., HIPAA-compliant) manner.

In an example illustrated in FIG. 10A, the treatment device 1000 is shown including an auricular component 1002 connected via a connector to a pulse generator 1004, and the pulse generator 1004 is wirelessly connected to the peripheral device(s) 1010 and/or the network 1020. This configuration, for example, may enable a patient, caregiver, or clinical user to adjust settings and/or monitor treatment controlled by the pulse generator 1004. For example, an application running on a peripheral device 1010 may provide one or more adjustable controls to the user for adjusting the delivery of therapy by the pulse generator 1004 to the patient via the auricular component 1002. Further, feedback data gathered by the auricular component 1002 and/or the pulse generator 1004, such as sensor feedback, may be supplied by the pulse generator 1004 to one or more of the peripheral devices 1010. The feedback, for example, may include sensor signals related to symptoms of the patient being treated by the treatment device 1000. A clinical user monitoring sensor metrics related to these signals may manually adjust the delivery of therapy accordingly using the one or more adjustable controls provided by the application. Further, in some implementations, the feedback may be used by one of the peripheral devices 1010 to generate a notification for review by the patient, a caregiver, or a clinician. The notification, for example, may include a low power notification, a device removed notification, or a malfunction notification. In an illustrative example, the treatment device 1000 may monitor impedance measurements allowing closed-loop neurostimulation. The notifications regarding removal or malfunction, for example, may be issued upon determining that the impedance measurements are indicative of lack of a proper contact between one or more electrodes of the treatment device 1000 and tissue on or surrounding the patient's ear. The notifications, for example, may be delivered to the patient and/or one or more third parties via an application executing on one of the peripheral devices 1010. For example, the application may issue an audible alarm, present a visual notification, or generate a haptic output on the peripheral device 1010. Further, in some embodiments, the application may issue a notification via a communication means, such as sending an email, text message, or other electronic message to one or more authorized users, such as a patient, caregiver, and/or clinician.

Conversely, in some implementations, the configuration illustrated in FIG. 10A enables automatic adjustment of therapy delivery by reviewing feedback provided by the treatment device 1000 and/or one or more peripheral devices 1010 (e.g., fitness monitors and/or health monitors used by the patient). In one example, a cloud platform accessible via the network 1020 may receive the feedback, review present metrics, and relay instructions to the pulse generator 1004 (e.g., via a Wi-Fi network or indirectly via a local portable device belonging to the patient such as a smart phone app in communication with the treatment device 1000). The pulse generator 1004, in a further example, may gather feedback from the one or more fitness monitor and/or health monitor devices 1010, analyze the feedback, and determine whether to adjust treatment accordingly.

Turning to FIG. 10B, in some implementations, the auricular component 1002 of the treatment device 1000 may further be enabled for wireless transmission of information with one or more peripheral devices 1010. For example, the auricular component 1002 may include a short-range radio frequency transmitter for sharing sensor data, alerts, error conditions, or other information with one or more peripheral devices 1010. The data, for example, may be collected in a small non-transitory (e.g., non-volatile) memory region built into the auricular component 1002.

In other implementations, the pulse generator 1004 is included in the auricular component 1002 that is, they are co-located thus the need for an extension cable to connect them is not necessary. The auricular component 1002 and pulse generator 1004 may be wirelessly connected to an electronic device (for example a personal computer, a tablet or a phone) 1010 and/or to a remote server 1010 via the network 1020. In turn, in some embodiments, the electronic device 1010 is also wirelessly connected to a remote server via the network 1020.

As shown in FIG. 10C, different communication components of the treatment device 1000 can be in communication with the peripheral device(s) 1010 or network 1020. In some implementations, the treatment device 1000 includes at least one isolated port 1032 for wired communication with the peripheral device 1010. The isolated port 1032, in some examples, may be a universal serial bus (USB) connection (e.g., a mini-USB connection, a micro-USB connection, a USB-C port, etc.), an Ethernet port, or a Serial ATA (SATA) connector. The isolated port 1032, for example, may be included in the pulse generator 1004 for updating a software version running on the pulse generator 1004 or for reprogramming treatment settings of the pulse generator 1004. The isolated port(s) 1032 may be connected to a communications port engine 1034 for enabling communications between a peripheral device 1010 and the treatment device 1000 via the isolated port 1032. The communications port engine 1034 may couple the isolated port 1032 to one or more microprocessors 1036. For example, the communications port engine 1034 may establish a direct (e.g., wired) communication link with one of the peripheral devices 1010 to transfer data from a memory 1038 to the peripheral device 1010.

Further, a wireless radio frequency (RF) antenna (e.g., transmitter or transmitter/receiver) 1040, in some implementations, is included in the treatment device 1000. The RF antenna 1040 can be in wireless communication with the peripheral device(s) 1010 directly or via the network 1020. The RF antenna 1040, in combination with processing circuitry for generating wireless communications (e.g., another communication port engine 1034 or a portion of the microprocessor(s) 1036) may function as a broadcast antenna, providing information to any RF receiver in a receiving region of the treatment device 1000. For example, the RF antenna 1040 may broadcast sensor data, sensor metrics, alerts, alarms, or other operating information for receipt by one or more peripheral devices 1010. In other implementations, the RF antenna 1040, in combination with additional processing circuitry, may establish a wireless communication link with a particular peripheral device 1010. The wireless communication link, in some embodiments, is a secure wireless communication link (e.g., HIPAA-compliant) for sharing patient data with the peripheral device(s) 1010. The wireless communication link may be used to receive control settings from a peripheral device 1010 for controlling the functionality of the pulse generator 1004, for example.

Figure 11:
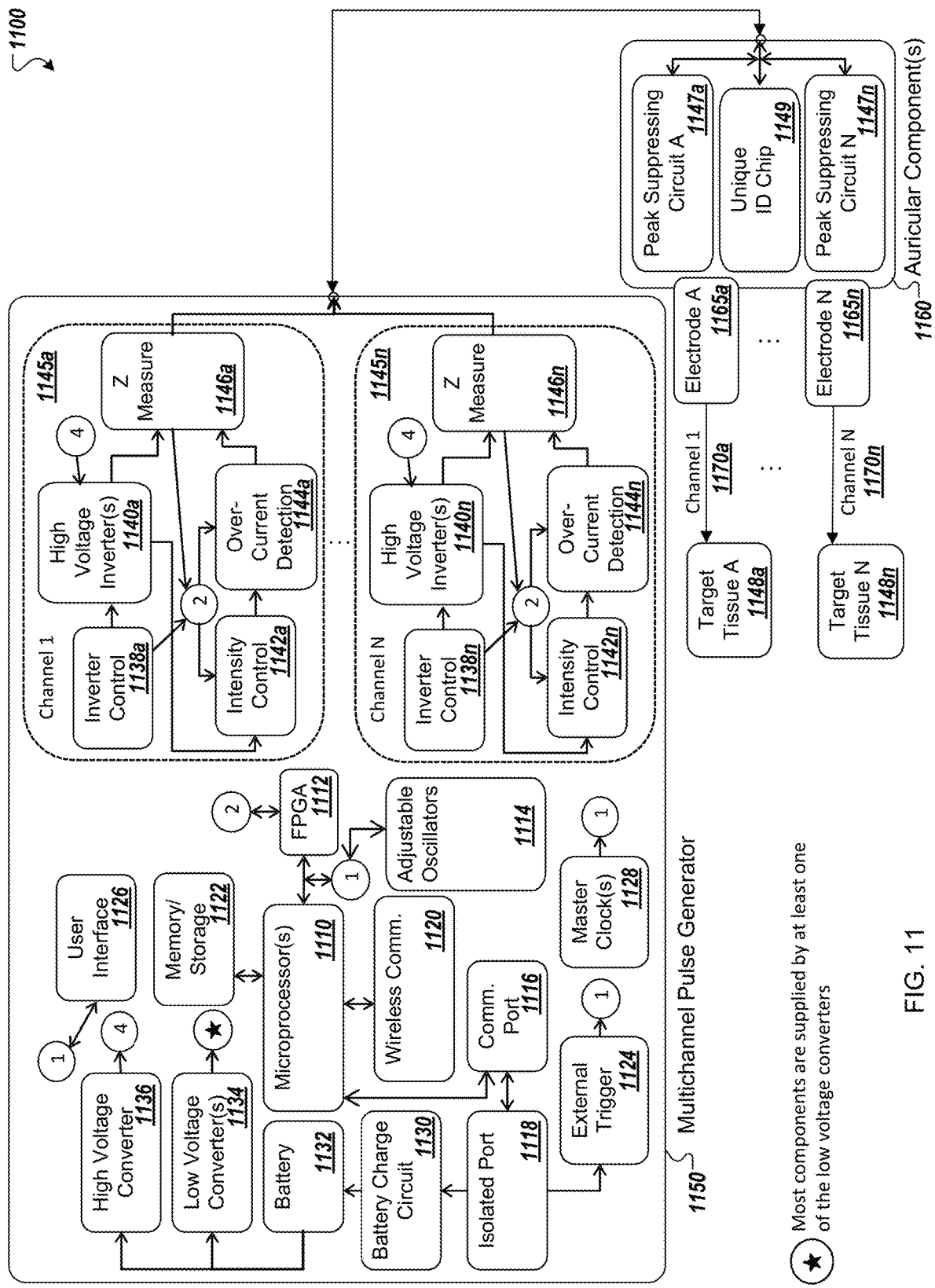
FIG. 11 is a block diagram of components of an example pulse generator in communication with an example auricular therapy device.

Turning to FIG. 11, a schematic 1100 of components of a multichannel pulse generator 1150 in communication with components of the flexible PCB 1160 of the auricular component is shown according to an example. The multichannel pulse generator circuit 1150 has at least one microcontroller or a microprocessor 1110 with at least one core.

When multiple microcontrollers or multiple cores are present, for example one controls the radio 1120 and other core(s) are dedicated to control the therapy. In one embodiment, a low power programmable logic circuitry (e.g., FPGA or PLD) 1112 is also available such that the microcontroller 1110 goes into a low power mode as much as possible while the programmable logic circuitry 1112 controls therapy delivery.

In some embodiments, an inverter circuit 1140 is used to generate biphasic/bipolar pulses. In some embodiments, one inverter circuit is use per channel, while in other embodiment, a single inverter is used for multiple channels. In one embodiment, each channel targets a different anatomical area 1148. A high voltage compliance (e.g., >50V, in other embodiments >70V, and yet in others >90V) may be used to ensure there is enough margin on the electrical potential to generate current demanded by the intensity control 1142. In order to enhance safety, in some embodiments an over current detection circuit 1144 is present. In one embodiment an impedance measuring circuit is present 1146, such that impedance can be tracked over time and to identify when the electrodes are not in contact or in good contact with the skin or if the cable is disconnected, or if the electrodes have deteriorated or are defective. Monitoring impedance over time provides the added advantage that the condition of the contact electrode can be followed; thus allowing the circuit to alert the user when the contact electrodes are close to their end of life or no longer viable.

In some embodiments, an isolated port 1118, such as a USB is used to charge the battery, and to communicate with the microcontroller(s) 1110. The communication can be both ways, such that instructions or entire new code can be uploaded to the microcontroller(s) 1110 and to download information stored in the memory 1122. In some embodiments, memory 1122 can be added to the circuit as an external CHIP, while in other embodiments, the memory 1122 can be internal to the microcontroller(s) 1110. In some embodiments, the FPGA 1112 may also have internal memory. In some embodiments, an external trigger circuit 1124 is included, such that the stimulation can be started and/or stopped via an external signal. In some embodiments, the external trigger signal can be passed through the isolated port 1118; in yet other embodiments a modified USB configuration (i.e., not using the standard USB pin configuration) can be used to pass the trigger signal. Using a modified USB configuration will force a custom USB cable to be used, thus ensuring that an external trigger cannot be provided by mistake using an off-the-shelf USB cable.

In some embodiments, a hardware user interface 1126 is used to interact with the circuit. In an example, the user interface 1126 can comprise of buttons, LEDs, haptic (e.g., piezoelectric) devices such as buzzers, and/or a display, or a combination of any of them.

In some embodiments, an external master clock 1128 is used to drive the microcontroller(s) 1110 and/or the FPGA 1112, in other embodiments the clock(s) 1128 can be internal or integrated or co-packaged with the microcontroller(s) 1110 and/or the FPGA 1112. In some embodiments, one or more oscillators, including in some cases adjustable oscillators 1114 are used to set pulse parameters such as for example, frequency and/or pulse width.

In some embodiments, the auricular component 1160 is made from a thin flex PCB or printed electronics, such that it is light weight and can be easily bent to accommodate different anatomies. In some embodiments, the auricular circuit 1160 has more than one channel. In one embodiment, each channel includes a peak suppressing circuit 1147 and electrodes 1148 to contact the skin at the location of the target tissue. In some embodiments, the auricular circuit 1160 includes a unique chip identifier or unique ID chip 1149. The unique ID chip 1149 can be used to track usage as well as to prevent other no authorized circuits to be connected to the multichannel pulse generator 1150. At least one auricular circuit 1160 is connected to the multichannel pulse generator 1150.

In an exemplary embodiment, the system utilizes feedback to monitor and/or modify the therapy. The feedback may be obtained from one or more sensors capable of monitoring one or more symptoms being treated by the therapy. For example, upon reduction or removal of one or more symptoms, a therapeutic output may be similarly reduced or ceased. Conversely, upon increase or addition of one or more symptoms, the therapeutic output may be similarly activated or adjusted (increased, expanded upon, etc.). In some examples, the sensors may monitor one or more of electrodermal activity (e.g., sweating), movement activity (e.g., tremors, physiologic movement), glucose level, neurological activity (e.g., via EEG), and/or cardiopulmonary activity (e.g., EKG, heart rate, blood pressure (systolic, diastolic and mean)). Imaging techniques such as MRI and fMRI could be used to adjust the therapy in a clinical setting for a given user. In other embodiments, imaging of pupillary changes (e.g., pupillary dilation) using, for example a common cellular phone and/or smart-glass glasses could be used to provide feedback to make therapy adjustments. In some implementations, one or more sensors are integrated into the earpiece and/or concha apparatus. One or more sensors, in some implementations, are integrated into the pulse generator. For example, periodic monitoring may be achieved through prompting the wearer to touch one or more electrodes on the system (e.g., electrodes built into a surface of the pulse generator) or otherwise interact with the pulse generator (e.g., hold the pulse generator extended away from the body to monitor tremors using a motion detector in the pulse generator). In further implementations, one or more sensor outputs may be obtained from external devices, such as a fitness computer, smart watch, or wearable health monitor.

The monitoring used may be based, in part, on a treatment setting. For example, EEG monitoring is easier in a hospital setting, while heart rate monitoring may be achieved by a sensor such as a pulsometer built into the earpiece or another sensor built into a low budget health monitoring device such as a fitness monitoring device or smart watch.

In an illustrative example, feedback related to electrodermal activity could be used to monitor and detect a speed or timing of a symptom and/or therapeutic outcome. In an example, the electrodermal activity could be sensed by electrodes on the therapeutic earpiece device. In another example, the electrodermal activity could be detected by electrodes on another portion of the body and communicated to the system.

In some implementations, the system can further include one or more motion detectors, such as accelerometers or gyroscopes, that can be used gather information to modulate the therapy. In an example, the one or more motion detectors are configured to detect a tremor and/or physiologic movement. In an aspect, the tremor and/or the physiologic movement can be indicative of the underlying condition and/or the treatment to the underlying condition. In an example, the tremor and/or physiologic movement can be indicative of symptoms associated with substance withdrawal. In an aspect, feedback from glucose monitoring can be used to modulate the therapy.

In yet other implementations, EKG can be used to assess heart rate and heart rate variability, to determine the activity of the autonomic nervous system in general and/or the relative activity of the sympathetic and parasympathetic branches of the autonomic nervous system, and to modulate the therapy. Autonomic nervous activity can be indicative of symptoms associated with substance withdrawal. In an aspect, the treatment device can be used to provide therapy for treating cardiac conditions such as atrial fibrillation and heart failure. In an example, therapy can be provided for modulation of the autonomic nervous system. In some implementations, the treatment device can be used to provide therapy to balance a ratio between any combinations of the autonomic nervous system, the parasympathetic nervous system, and the sympathetic nervous system.

In an aspect, the system can monitor impedance measurements allowing closed-loop neurostimulation. In an example, monitoring feedback can be used to alert patient/caregiver if therapy is not being adequately delivered and if the treatment device is removed.

Reference has been made to illustrations representing methods and systems according to implementations of this disclosure. Aspects thereof may be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/operations specified in the illustrations.

One or more processors can be utilized to implement various functions and/or algorithms described herein. Additionally, any functions and/or algorithms described herein can be performed upon one or more virtual processors, for example on one or more physical computing systems such as a computer farm or a cloud drive.

Aspects of the present disclosure may be implemented by hardware logic (where hardware logic naturally also includes any necessary signal wiring, memory elements and such), with such hardware logic able to operate without active software involvement beyond initial system configuration and any subsequent system reconfigurations. The hardware logic may be synthesized on a reprogrammable computing chip such as a field programmable gate array (FPGA), programmable logic device (PLD), or other reconfigurable logic device. In addition, the hardware logic may be hard coded onto a custom microchip, such as an application-specific integrated circuit (ASIC). In other embodiments, software, stored as instructions to a non-transitory computer-readable medium such as a memory device, on-chip integrated memory unit, or other non-transitory computer-readable storage, may be used to perform at least portions of the herein described functionality.

Various aspects of the embodiments disclosed herein are performed on one or more computing devices, such as a laptop computer, tablet computer, mobile phone or other handheld computing device, or one or more servers. Such computing devices include processing circuitry embodied in one or more processors or logic chips, such as a central processing unit (CPU), graphics processing unit (GPU), field programmable gate array (FPGA), application-specific integrated circuit (ASIC), or programmable logic device (PLD). Further, the processing circuitry may be implemented as multiple processors cooperatively working in concert (e.g., in parallel) to perform the instructions of the inventive processes described above The process data and instructions used to perform various methods and algorithms derived herein may be stored in non-transitory (i.e., non-volatile) computer-readable medium or memory. The claimed advancements are not limited by the form of the computer-readable media on which the instructions of the inventive processes are stored. For example, the instructions may be stored on CDs, DVDs, in FLASH memory, RAM, ROM, PROM, EPROM, EEPROM, hard disk or any other information processing device with which the computing device communicates, such as a server or computer. The processing circuitry and stored instructions may enable the pulse generator 1004 of FIG. 10A through FIG. 10C or the pulse generator 1150 of FIG. 11 to perform various methods and algorithms described above. Further, the processing circuitry and stored instructions may enable the peripheral device(s) 1010 of FIG. 10A through FIG. 10C to perform various methods and algorithms described above.

These computer program instructions can direct a computing device or other programmable data processing apparatus to function in a particular manner, such that the instructions stored in the computer-readable medium produce an article of manufacture including instruction means which implement the function/operation specified in the illustrated process flows.

Embodiments of the present description rely on network communications. As can be appreciated, the network can be a public network, such as the Internet, or a private network such as a local area network (LAN) or wide area network (WAN) network, or any combination thereof and can also include PSTN or ISDN sub-networks. The network can also be wired, such as an Ethernet network, and/or can be wireless such as a cellular network including EDGE, 3G, 4G, and 5G wireless cellular systems. The wireless network can also include Wi-Fi, Bluetooth, Zigbee, or another wireless form of communication. The network, for example, may be the network 1020 as described in relation to FIGS. 10A through 10C.

The computing device, such as the peripheral device(s) 1010 of FIGS. 10A through 10C, in some embodiments, further includes a display controller for interfacing with a display, such as a built-in display or LCD monitor. A general purpose I/O interface of the computing device may interface with a keyboard, a hand-manipulated movement tracked I/O device (e.g., mouse, virtual reality glove, trackball, joystick, etc.), and/or touch screen panel or touch pad on or separate from the display.

A sound controller, in some embodiments, is also provided in the computing device, such as the peripheral device(s) 1010 of FIGS. 10A through 10C, to interface with speakers/microphone thereby providing audio input and output.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry or based on the requirements of the intended back-up load to be powered.

Certain functions and features described herein may also be executed by various distributed components of a system. For example, one or more processors may execute these system functions, where the processors are distributed across multiple components communicating in a network such as the network 1020 of FIGS. 10A through 10C. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process.

Although provided for context, in other implementations, methods and logic flows described herein may be performed on modules or hardware not identical to those described. Accordingly, other implementations are within the scope that may be claimed.

In some implementations, a cloud computing environment, such as Google Cloud Platform™, may be used perform at least portions of methods or algorithms detailed above. The processes associated with the methods described herein can be executed on a computation processor of a data center. The data center, for example, can also include an application processor that can be used as the interface with the systems described herein to receive data and output corresponding information. The cloud computing environment may also include one or more databases or other data storage, such as cloud storage and a query database. In some implementations, the cloud storage database, such as the Google Cloud Storage, may store processed and unprocessed data supplied by systems described herein.

The systems described herein may communicate with the cloud computing environment through a secure gateway. In some implementations, the secure gateway includes a database querying interface, such as the Google BigQuery platform.

While certain embodiments have been described, these embodiments have been presented by way of example only and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A neurostimulation apparatus for controlling or reducing stress levels while avoiding decreasing vagal tone, the neurostimulation apparatus comprising:
   an ear-mounted stimulation device comprising
      an earpiece configured to be positioned over an ear of a wearer in contact with tissue regions surrounding the ear of the wearer, and
      a plurality of electrodes each configured to deliver a non-piercing electrical stimulation via skin,
      wherein a first one or more electrodes of the plurality of electrodes is arranged on a first surface of the earpiece configured to contact a first tissue region of the tissue regions, wherein at least one of an auricular branch of a vagus nerve (ABVN) or an auriculotemporal nerve (ATN) is situated directly beneath and/or beneath and closely adjacent to the first tissue region, and
      wherein a second one or more electrodes of the plurality of electrodes are arranged on a second surface of the ear-mounted stimulation device configured to contact a second tissue region of the tissue regions; and a controller in electrical communication with the ear-mounted stimulation device, the controller comprising processing circuitry configured to deliver therapeutic stimulation pulses configured to control or reduce stress levels via the ear-mounted stimulation device, wherein delivering the therapeutic stimulation pulses comprises delivering a first series of stimulation pulses to the first one or more electrodes at one or more frequencies within a range from 5 Hz to 30 Hz, wherein the first series of stimulation pulses is configured to increase activity in a parasympathetic nervous system (PNS), and delivering a second series of stimulation pulses to the second one or more electrodes at one or more frequencies within a range from 70 Hz to 150 Hz, wherein the therapeutic stimulation pulses in combination with positioning of the first one or more electrodes to contact the first tissue region and positioning of the second one or more electrodes to contact the second tissue region are configured to modulate an activity ratio between a sympathetic nervous system (SNS) and the PNS, thereby increasing vagal tone.

2. The neurostimulation apparatus of claim 1, wherein an in-ear portion of the ear-mounted stimulation device comprises the second surface of the ear-mounted stimulation device.

3. The neurostimulation apparatus of claim 2, wherein the in-ear portion is in wired electrical communication with the earpiece.

4. The neurostimulation apparatus of claim 1, wherein the first tissue region is adjacent to an auricle of the ear.

5. The neurostimulation apparatus of claim 1, wherein each electrode of the first one or more electrodes is disposed, when the ear-mounted stimulation device is worn by the wearer, in a respective position against respective tissue of an external portion of the ear or respective tissue surrounding the external portion of the ear.

6. The neurostimulation apparatus of claim 1, wherein the second tissue region is an in-ear tissue region.

7. The neurostimulation apparatus of claim 6, wherein each electrode of the second one or more electrodes is disposed, when the ear-mounted stimulation device is worn by the wearer, in a respective position against respective tissue of a concha, cavum, or a tragus of the ear.

8. The neurostimulation apparatus of claim 1, wherein the second series of neural pathway stimulation pulses is configured to increase responsiveness of the wearer to sensory inputs.

9. The neurostimulation apparatus of claim 1, wherein the second series of neural pathway stimulation pulses is configured to promote wakefulness, promote alertness, and/or mitigate fatigue in the wearer.

10. The neurostimulation apparatus of claim 1, wherein the second series of neural pathway stimulation pulses is configured to increase cognitive processing of the wearer.

11. The neurostimulation apparatus of claim 1, wherein the therapeutic stimulation pulses are configured to mitigate stress including acute stress, Acute Stress Reaction, Combat Stress Reaction, and/or Operational Stress Reaction.

12. The neurostimulation apparatus of claim 1, wherein delivery of the therapeutic stimulation pulses is intermittently activated to control stress, thereby mitigating symptoms leading to chronic stress.

13. The neurostimulation apparatus of claim 1, wherein the controller is in wired electrical communication with the ear-mounted stimulation device.

14. The neurostimulation apparatus of claim 1, wherein an external pulse generator comprises the controller.

15. The neurostimulation apparatus of claim 1, wherein:
the ear-mounted stimulation device is disposable; and
the controller is releasably attachable to the ear-mounted stimulation device.

16. The neurostimulation apparatus of claim 1, wherein delivering the therapeutic stimulation pulses comprises activating the therapeutic stimulation pulses intermittently for a plurality of time intervals over a usage time period of at least thirty minutes, wherein a duration of each time interval is at least five minutes.

* * * * *